United States Patent
Yasuda et al.

(10) Patent No.: US 8,877,457 B2
(45) Date of Patent: Nov. 4, 2014

(54) DEVICE FOR EXAMINING MYOCARDIAL TOXICITY, CHIP FOR EXAMINING MYOCARDIAL TOXICITY AND METHOD FOR EXAMINING MYOCARDIAL TOXICITY

(75) Inventors: Kenji Yasuda, Bunkyo-ku (JP); Atsushi Sugiyama, Bunkyo-ku (JP); Tomoyuki Kaneko, Bunkyo-ku (JP); Fumimasa Nomura, Bunkyo-ku (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 627 days.

(21) Appl. No.: 13/132,781

(22) PCT Filed: Dec. 4, 2009

(86) PCT No.: PCT/JP2009/070382
§ 371 (c)(1),
(2), (4) Date: Jul. 14, 2011

(87) PCT Pub. No.: WO2010/064700
PCT Pub. Date: Jun. 10, 2010

(65) Prior Publication Data
US 2011/0262958 A1  Oct. 27, 2011

(30) Foreign Application Priority Data
Dec. 5, 2008 (JP) ................. 2008-311341

(51) Int. Cl.
*C12Q 1/02* (2006.01)
*C12M 1/34* (2006.01)
*C12M 3/00* (2006.01)
*G01N 33/50* (2006.01)

(52) U.S. Cl.
CPC ........ *G01N 33/5014* (2013.01); *C12N 2503/02* (2013.01); *G01N 33/5061* (2013.01)
USPC ................ 435/29; 435/287.1; 435/288.7

(58) Field of Classification Search
CPC .......... G01N 33/5061; G01N 33/5014; C12N 2503/02
See application file for complete search history.

(56) References Cited

U.S. PATENT DOCUMENTS

| 7,569,354 B2 | 8/2009 | Okano et al. |
| 2004/0009566 A1 | 1/2004 | Okano et al. |

(Continued)

FOREIGN PATENT DOCUMENTS

| EP | 1 901 067 A2 | 3/2008 |
| EP | 2157165 A1 | 2/2010 |

(Continued)

OTHER PUBLICATIONS

Extended European Search Report dated Aug. 9, 2012 issued in corresponding European Patent Application No. 09830466.0.

(Continued)

Primary Examiner — Nathan Bowers
Assistant Examiner — Gautam Prakash
(74) Attorney, Agent, or Firm — Sughrue Mion, PLLC

(57) ABSTRACT

Provided is a device and a method for examining myocardial toxicity, which can be realized in vitro in an equivalent manner as those conventionally carried out in vivo. A cell population as a pulsating pacemaker is arranged on a transparent substrate. Myocardial pulsating cells are arranged while being spaced apart appropriately. Fibroblast cells are arranged with/connected to the myocardial pulsating cells to form a cell network. Each of the myocardial pulsating cells and fibroblast cells forming the network is arranged on a transparent electrode provided on the transparent substrate. The cells forming the network are exposed to a flow of a solution containing a drug and QT delay due to the drug is evaluated.

11 Claims, 15 Drawing Sheets
(9 of 15 Drawing Sheet(s) Filed in Color)

(56) References Cited

U.S. PATENT DOCUMENTS

2007/0059763 A1* 3/2007 Okano et al. .................. 435/7.1
2010/0178692 A1* 7/2010 Yasuda et al. ............. 435/288.7

FOREIGN PATENT DOCUMENTS

| EP | 2157166 A1 | 2/2010 |
|---|---|---|
| JP | 2006-094703 A | 4/2006 |
| JP | 2006-112846 A | 4/2006 |
| WO | 0208387 | 1/2002 |
| WO | 2005082280 | 9/2005 |
| WO | 2005107644 | 11/2005 |
| WO | 2008/152983 A1 | 12/2008 |

OTHER PUBLICATIONS

T. Kaneko, et al., "Dependence of the community effect of cultured cardiomyocytes on the cell network pattern", Biochemical and Biophysical Research Communications, Academic Press Inc. vol. 356, No. 2, Apr. 4, 2007, pp. 494-498, XP022090800, ISSN: 0006-291X.

T. Kaneko, et al., "An on-chip cardiomyocyte cell network assay for stable drug screening regarding community effect of cell network size", Analyst, Royal Society of Chemistry, GB, vol. 132, No. 9, Sep. 1, 2007, pp. 892-898, XP008125220, ISSN: 0003-2654.

International Search Report of PCT/JP2009/070382 dated Jan. 12, 2010.

F. Nomura, et al., "Construction of the cardiomyocyte network model using On-chip cellomics technology," Reports of the Institute of Biomaterials and Bioengineering, Mar. 31, 2009, pp. 34-36, vol. 42, (in Japanese).

I. Suzuki, "Detection of tetanus-induced effects in linearly lined-up micropatterned neuronal networks: Application of a multi-electrode array chip combined with agarose microstructures," Biochemical and Biophysical Research Communications, 2007, pp. 470-475, vol. 356, Issue 2.

Au et al., "Interactive effects of surface topography and pulsatile electrical field stimulation on orientation and elongation of fibroblasts and cardiomyocytes", Biomaterials, 28(29):4277-4293 (2007).

Notice of Reasons for Rejection for Japanese Application No. 2008-311341 dated May 20, 2014.

* cited by examiner

Fig. 4
(a) Pulse of cell population
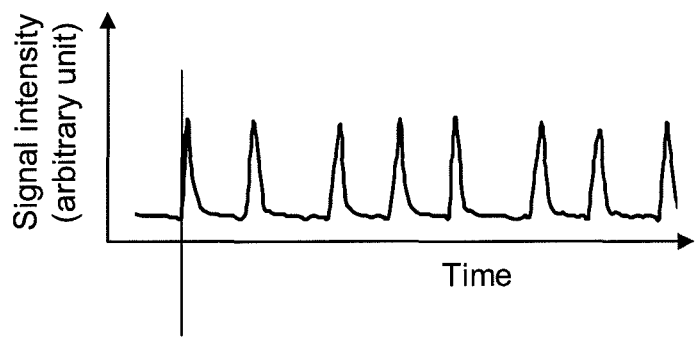
(b) Pulse of target cell (normal state)
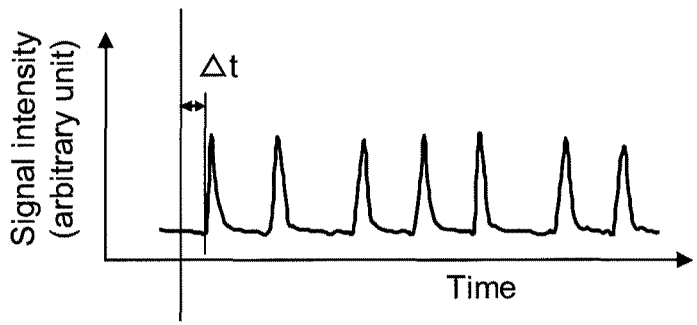
(c) Pulse of target cell (on-drug state)
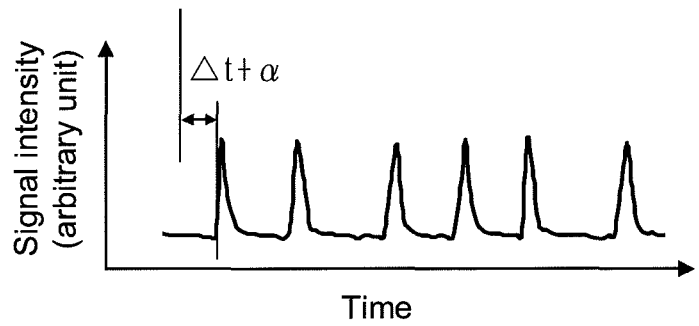

Fig. 5
(a) Changes in volume of cell due to pulsation of cell population
(b) Changes in volume of cell due to pulsation of target cell (normal state)
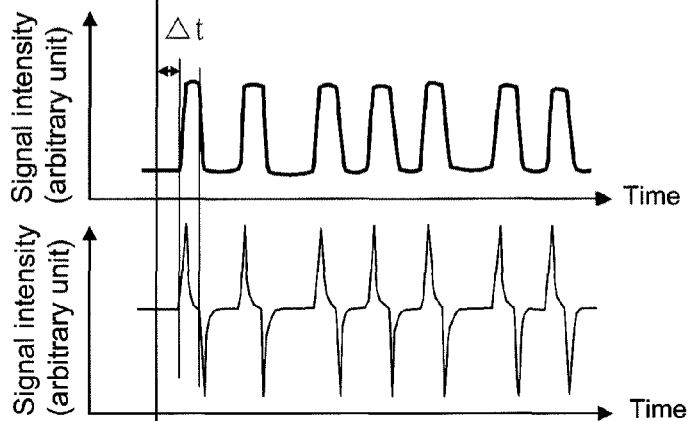
(c) Changes in volume of cell due to pulsation of target cell (on-drug state)
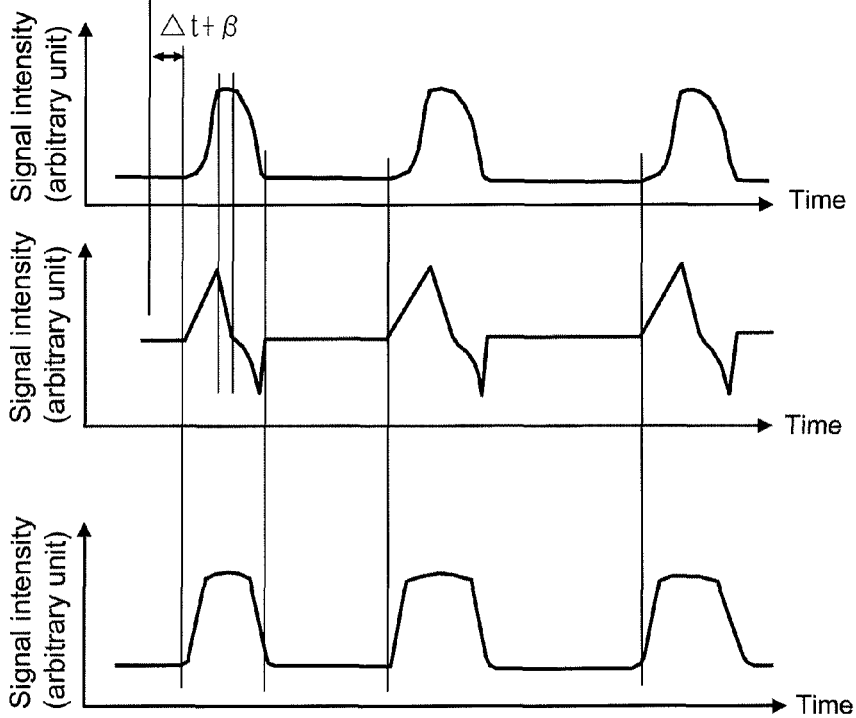

Fig. 6
(a) Changes in extracellular potentials of target cell (normal state)
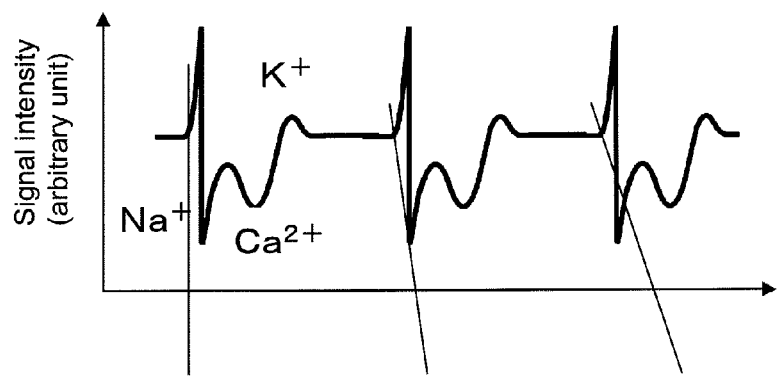
(b) Changes in extracellular potentials of target cell (on-drug state)
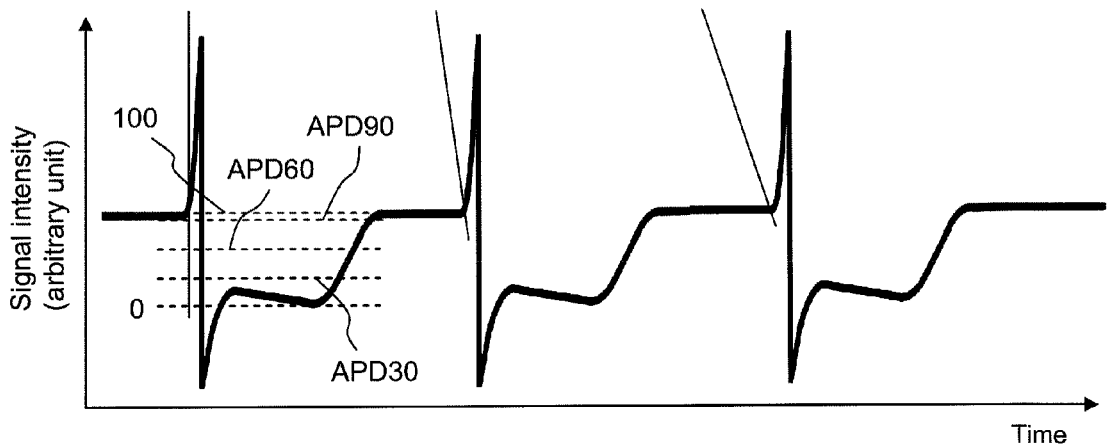

Fig. 9
(a)
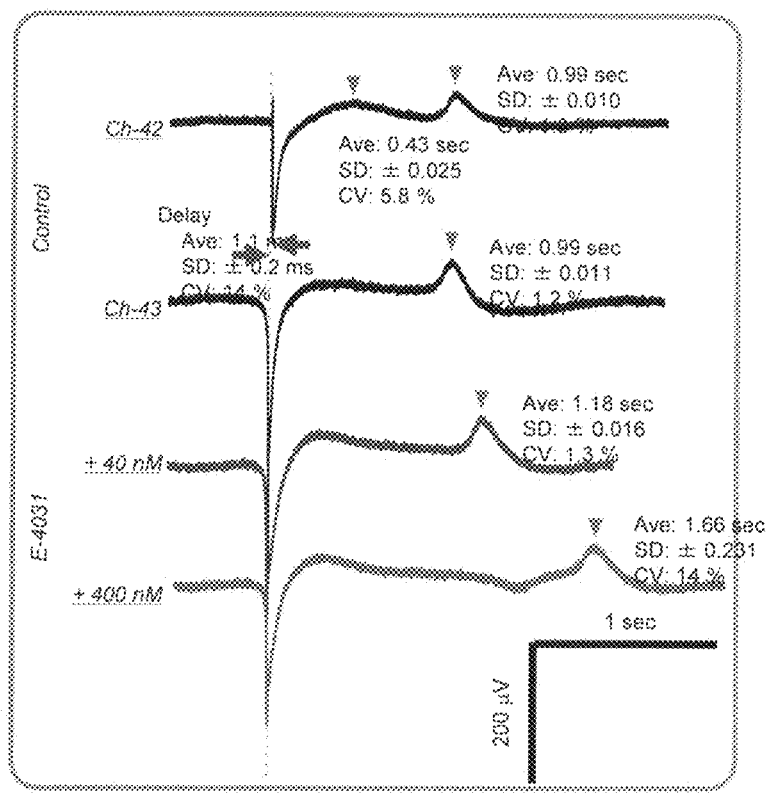
Convert FPD data into Poincare plots
(b)
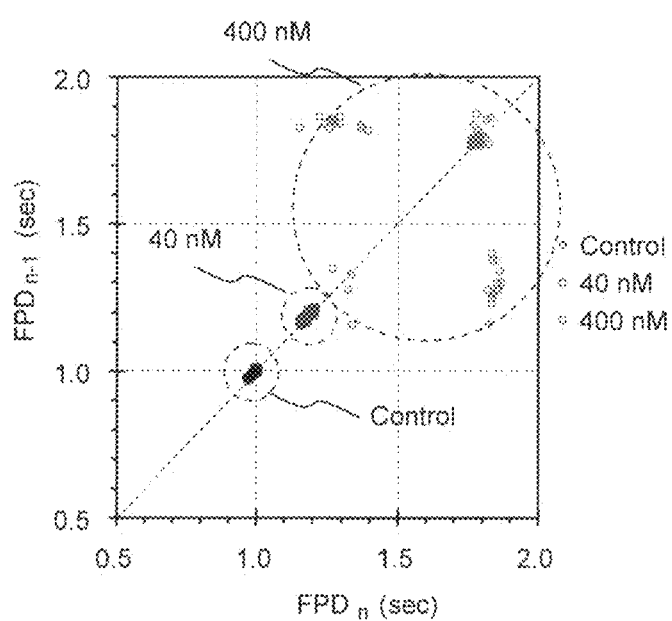

Fig. 10
(a) Number and arrangement of cells under control
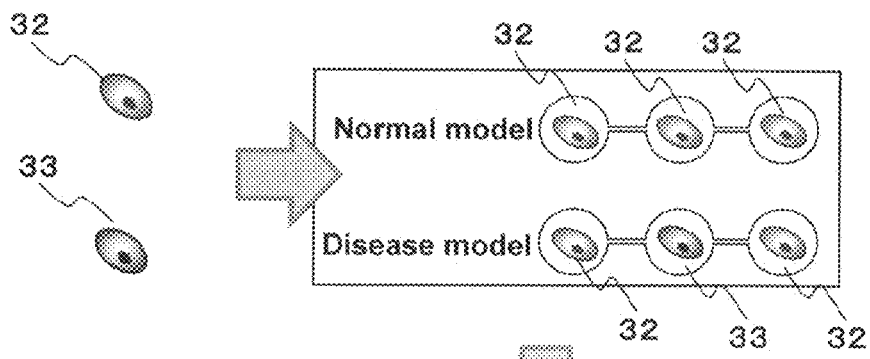
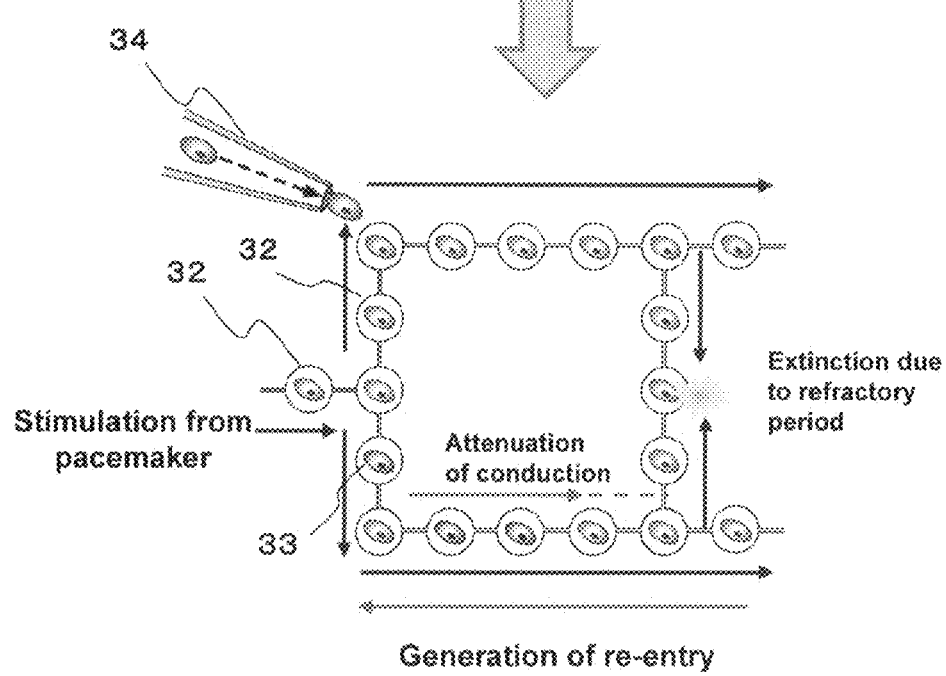
(b)

Fig. 11
(a)
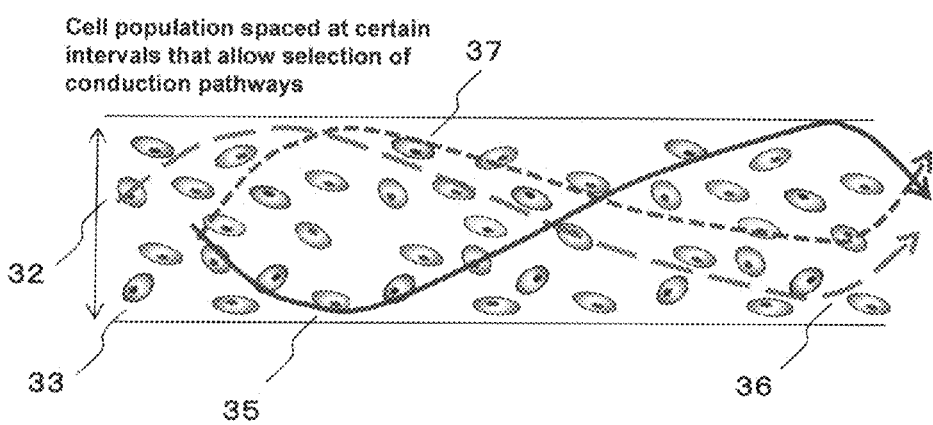
Cell population spaced at certain intervals that allow selection of conduction pathways
(b)
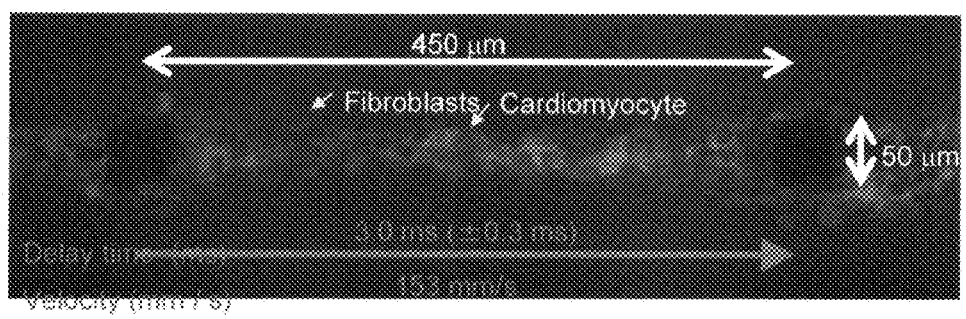
Chamber
  Length: 450 μm
  Width: about 50 μm
Total: 50 cells
  Myocyte: 32 cells
  Fibroblast: 18 cells
(c)
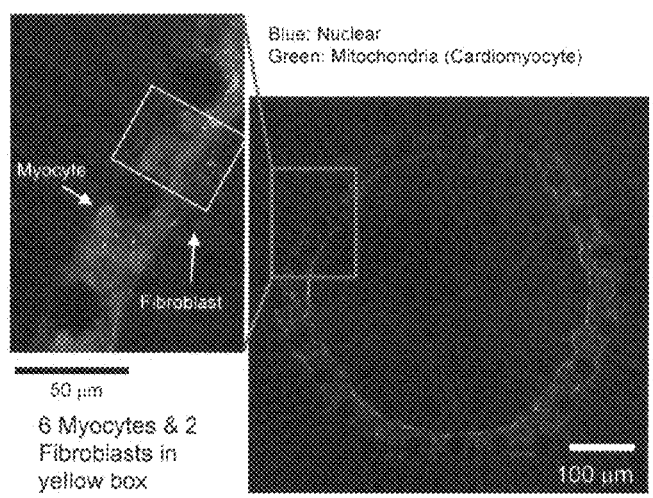
Blue: Nuclear
Green: Mitochondria (Cardiomyocyte)
6 Myocytes & 2 Fibroblasts in yellow box Fig. 12
(a)
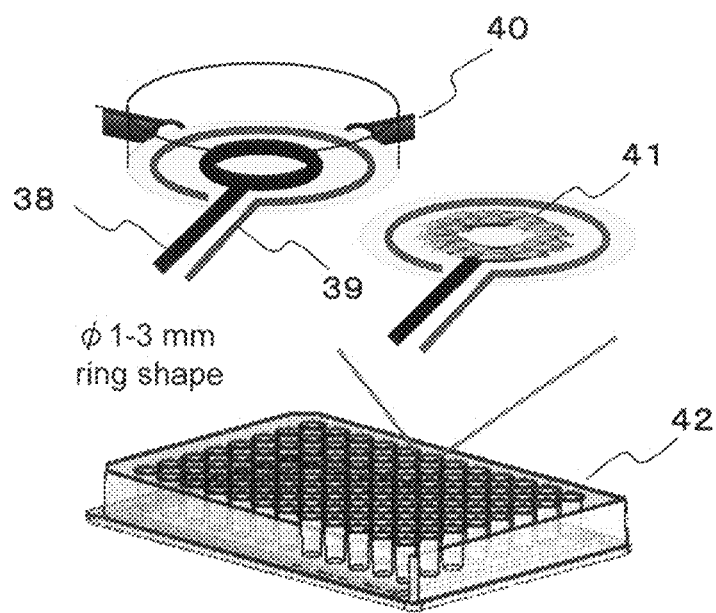
(b)
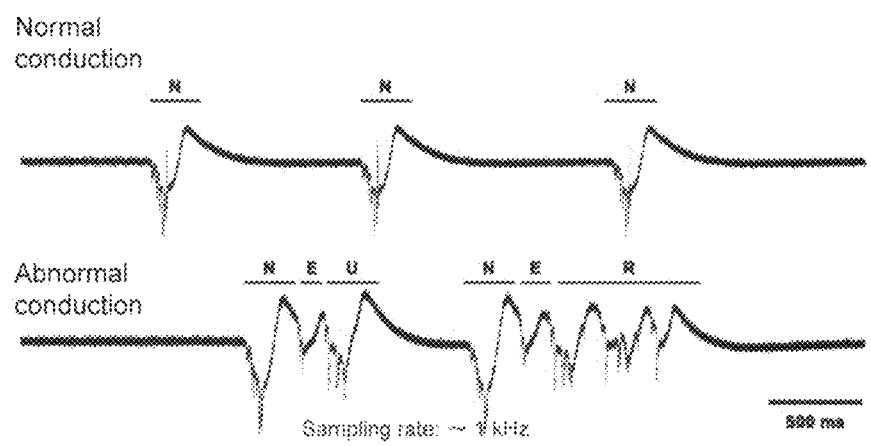

Fig. 13
(a)
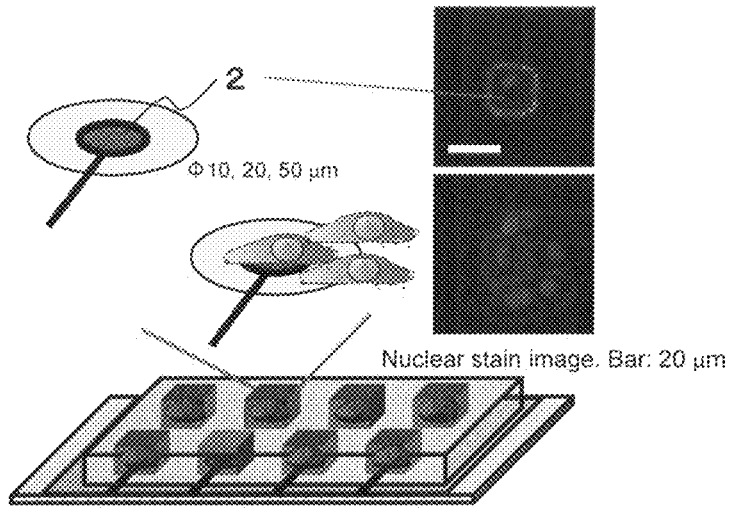
(b)
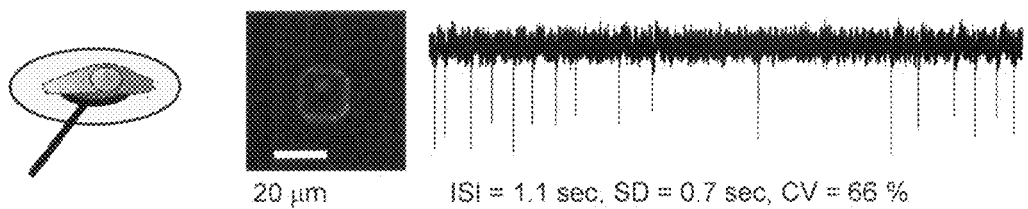
(c)
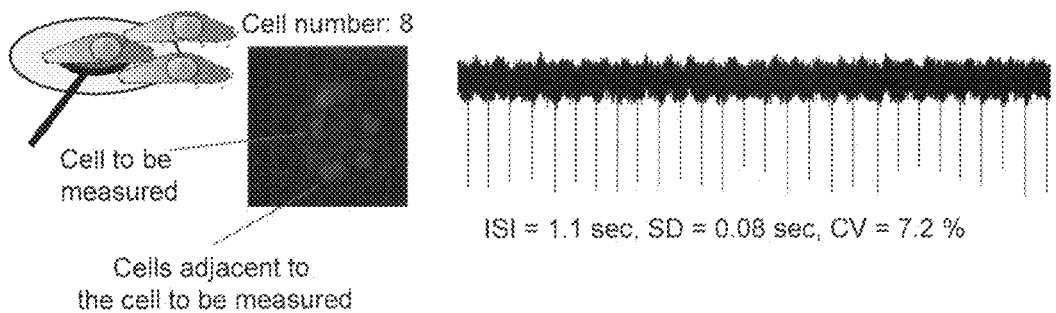

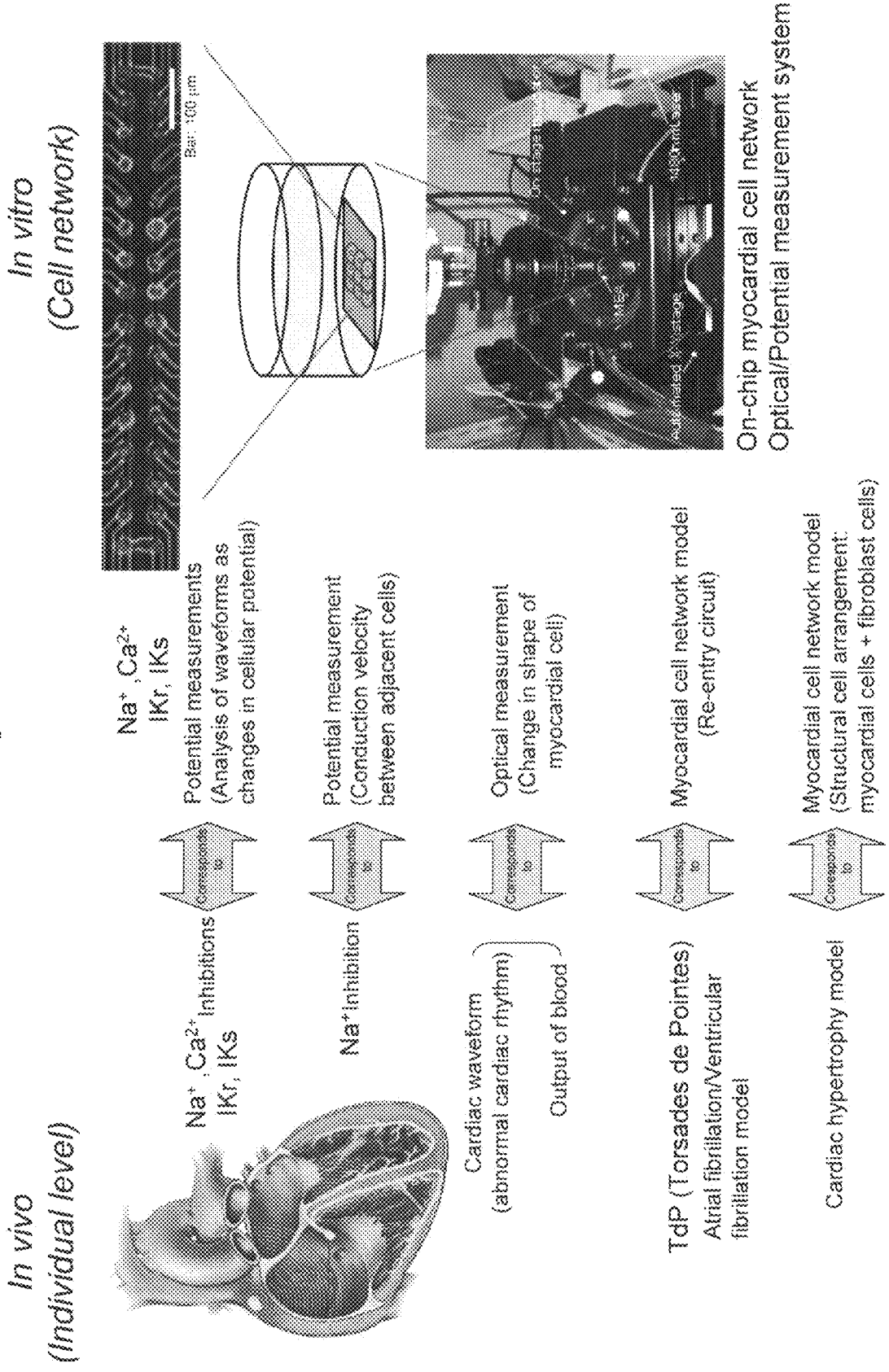

DEVICE FOR EXAMINING MYOCARDIAL TOXICITY, CHIP FOR EXAMINING MYOCARDIAL TOXICITY AND METHOD FOR EXAMINING MYOCARDIAL TOXICITY

CROSS REFERENCE TO RELATED APPLICATIONS

This application is a National Stage of International Application No. PCT/JP2009/070382 filed Dec. 4, 2009, claiming priority based on Japanese Patent Application No. 2008-311341 filed Dec. 5, 2008, the contents of all of which are incorporated herein by reference in their entirety.

TECHNICAL FIELD

The present invention relates to a device, a chip and a method for examining myocardial toxicity of a drug on a myocardial cell.

BACKGROUND ART

Bioassays are widely used for observing changes in a cellular state or response of a cell to a drug or the like. Conventional bioassays often employ culture cells. Since pluralities of cells are used in such a system to carry out an assay, an average value of the cell population is regarded as the property of a single cell.

In reality, however, cell cycles of cells of such a population hardly synchronize with each other, where respective cells express proteins at different cycles. Accordingly, there has always been a problem of fluctuation in analyzing the resulting responses to stimulation.

Specifically, since fluctuations are ubiquitously present in the response resulting from the reaction mechanisms of cells, only average response can be always obtained. In order to solve these problems, techniques such as synchronous culture have been developed. However, constant use of a group of cells at the same stage means to continuously supply such cells, which has been standing in the way of widely promoting bioassays.

In addition, since there are two types of stimulations (signals) given to a cell, i.e., those given depending on the amounts of signal molecules, nourishment and dissolved gas contained in the liquid around the cell, and those given due to physical contact/intercellular interaction with other cells, the situation has been difficult in order to judge the fluctuations.

The problems of physical contact/intercellular interaction between the cells can be solved to a certain degree by conducting a bioassay with a cell mass such as a tissue fraction. In this case, however, unlike culture cells, a cell mass with constant uniformity is not always available. Thus, there are problems of the resulting data being fluctuating or information being unnoticeable in such a population.

In order to measure an information processing model having each of the cells in a cell group as the minimum structural unit, the inventors of the present application have proposed, as described in Japanese Patent Laid-Open Application No. 2006-94703 (Patent document 1), a cell population microarray (bioassay chip) having a plurality of cell culture partitions for confining cells to particular spatial configurations, where adjacent partitions are connected via grooves or tunnels which do not allow cell passage therethrough, and, if necessary, a plurality of electrode patterns are applied to the grooves, tunnels or cell culture partitions for measuring changes in the potentials of the cells.

[Patent document 1] Japanese Patent Laid-Open Application No. 2006-94703

SUMMARY OF THE INVENTION

Problems to be Solved by the Invention

Conventional bioassays have treated cells either as a tissue fraction or as culture cells, i.e., a single cell. If the number of the cells is too large, as mentioned in the above section about conventional technique, the resulting information obtained would be averaged that may not accurately be reflecting the responses to a drug or the like. Use of one cell at a time means that said cell that normally functions as a cell of a multicellular tissue is used as a separated isolated cell and thus influence of the interaction between the cells would not be apparent, which again is problematic in obtaining accurate drug response, i.e., bioassay data.

With respect to myocardial cells and fibroblast cells, it is important to develop a device or a system that is capable of accurately measuring propagation of pulse from an adjacent myocardial cell or fibroblast cell as a cell potential or cell morphology on a single cell basis, and accurately examining toxicity of a drug on a myocardial cell measuring a cell potential or cell morphology of a single cell.

Means for Solving the Problems

With respect to the problems mentioned above, the present invention provides a device, a chip and a method described below for examining myocardial toxicity.

(1) A myocardial toxicity examining device comprising:
a transparent substrate;
a cell population comprising a plurality of stably-pulsating myocardial cells arranged on the transparent substrate;
a cell communication channel comprising a tandemly-arranged plurality of myocardial cells and fibroblast cells which conduct pulse from the cell population in cooperation with one of the cells of the cell population;
walls formed on the transparent substrate for filling around the cell population and the cell communication channel with a cell culture solution;
means for feeding and draining the cell culture solution into and from the region surrounded by the walls;
means for adding a drug that acts on the cells to the cell culture solution;
a microelectrode provided on the transparent substrate and having thereon one of the cells of the cell population;
a plurality of separate microelectrodes provided on the transparent substrate and having thereon some of the cells of the cell communication channel;
a comparison electrode provided within the region surrounded by the walls;
means for measuring and recording potentials of the cells on the microelectrodes by using readout lines connected to the respective microelectrodes and a readout line connected to the comparison electrode; and
means for optically measuring a state of one of the cells arranged on the transparent substrate.

(2) The myocardial toxicity examining device according to (1) above, wherein the cell is surrounded by non-cell-adherent walls with gaps that do not allow the cell to pass therethrough.

(3) The myocardial toxicity examining device according to (1) above comprising a barrier between the region provided with the cell population and the region provided with the cell communication channel, for blocking the flow of the cell culture solution, where the barrier is provided with an opening that allows cooperation between one of the cells of the cell population and the cell at the end of the cell communication channel.

(4) A myocardial toxicity examining device according to (1) above comprising means for adding a drug that acts on the cells to means for running the cell culture solution.

(5) A myocardial toxicity examining device comprising:
a transparent substrate;
a cell population comprising a plurality of cells arranged on the transparent substrate;
a cell communication channel comprising a tandemly-arranged plurality of myocardial cells and fibroblast cells which conduct pulse from the cell population in cooperation with one of the cells of the cell population;
walls formed on the transparent substrate for filling around the cell population and the cell communication channel with a cell culture solution;
means for feeding and draining the cell culture solution into and from the region surrounded by the walls;
means for adding a drug that acts on the cells to the cell culture solution;
a microelectrode provided on the transparent substrate and having thereon one of the cells of the cell population;
a plurality of separate microelectrodes provided on the transparent substrate and having thereon some of the cells of the cell communication channel;
a comparison electrode provided within the region surrounded by the walls;
means for measuring and recording potentials of the cells on the microelectrodes by using readout lines connected to the respective microelectrodes and a readout line connected to the comparison electrode; and
a stage for supporting the transparent substrate, which can be driven in the X-Y directions; and
means for optically measuring a state of the cell arranged on the transparent substrate supported by the stage.

(6) A myocardial toxicity examining device according to (5) above, wherein the cell is surrounded by non-cell-adherent walls with gaps that do not allow the cell to pass therethrough.

(7) The myocardial toxicity examining device according to (5) above comprising a barrier between the region provided with the cell population and the region provided with the cell communication channel, for blocking the flow of the cell culture solution, where the barrier is provided with an opening that allows cooperation between one of the cells of the cell population and the cell at the end of the cell communication channel.

(8) A myocardial toxicity examining device according to (5) above comprising means for adding a drug that acts on the cells to means for feeding the cell culture solution.

(9) A myocardial toxicity examining chip comprising:
a transparent substrate;
a cell population comprising a plurality of cells arranged on the transparent substrate;
a cell communication channel comprising a tandemly-arranged plurality of myocardial cells and fibroblast cells which conduct pulse from the cell population in cooperation with one of the cells of the cell population;
walls formed on the transparent substrate for filling around the cell population and the cell communication channel with a cell culture solution;
a microelectrode provided on the transparent substrate and having thereon one of the cells of the cell population;
a plurality of separate microelectrodes provided on the transparent substrate and having thereon some of the cells of the cell communication channel;
a comparison electrode provided within the region surrounded by the walls; and
readout lines connected to the respective microelectrodes and a readout line connected to the comparison electrode.

(10) The myocardial toxicity examining chip according to (9) above, wherein the cell is surrounded by non-cell-adherent walls with gaps that do not allow the cell to pass therethrough.

(11) The myocardial toxicity examining chip according to (9) above comprising a barrier between the region provided with the cell population and the region provided with the cell communication channel, for blocking the flow of the cell culture solution, where the barrier is provided with an opening that allows cooperation between one of the cells of the cell population and the cell at the end of the cell communication channel.

(12) A method for examining myocardial toxicity by using a myocardial toxicity examining device, said device comprising:
a transparent substrate;
a cell population comprising a plurality of stably-pulsating myocardial cells arranged on the transparent substrate;
a cell communication channel comprising a tandemly-arranged plurality of myocardial cells and fibroblast cells which conduct pulse from the cell population in cooperation with one of the cells of the cell population;
walls formed on the transparent substrate for filling around the cell population and the cell communication channel with a cell culture solution;
means for feeding and draining the cell culture solution into and from the region surrounded by the walls;
means for adding a drug that acts on the cells to the cell culture solution;
a microelectrode provided on the transparent substrate and having thereon one of the cells of the cell population;
a plurality of separate microelectrodes provided on the transparent substrate and having thereon some of the cells of the cell communication channel;
a comparison electrode provided within the region surrounded by the walls;
means for measuring and recording potentials of the cells on the microelectrodes by using readout lines connected to the respective microelectrodes and a readout line connected to the comparison electrode; and
means for optically measuring a state of one of the cells arranged on the transparent substrate,
wherein the method comprises the step of evaluating whether or not addition of a drug that acts on the cells to the cell culture solution delays the rate of the pulse generated by the cell population to propagate through the cell communication channel, thereby examining toxicity of the drug that acts on the cell on cardiac muscle.

(13) A myocardial toxicity examining device comprising:
a transparent substrate;
a myocardial cell population-retaining region comprising a plurality of cell holders ($CH_G$) provided on the transparent substrate for retaining stably-pulsating myocardial cells;
a cell communication channel comprising a tandemly-arranged plurality of cell holders ($CH_n$) each retaining a myocardial or fibroblast cell for conducting pulse from the myocardial cell population in cooperation with one of the cells of the cell holders;

a region for filling in a cell culture solution, defined by the surface of the transparent substrate and walls formed around the myocardial cell population-retaining region and the cell communication channel;

means for feeding and draining the cell culture solution into and from the region surrounded by the walls;

means for adding a drug that acts on the cells to the cell culture solution;

a microelectrode provided on the transparent substrate and having thereon a myocardial cell in one of the cell holders ($CH_G$) in the myocardial cell population-retaining region;

a plurality of microelectrodes provided on the transparent substrate and having thereon a myocardial or fibroblast cell in each of the plurality of the cell holders ($CH_n$) in the cell communication channel;

a comparison electrode provided within the region surrounded by the walls;

means for measuring and recording potentials of the cells on the microelectrodes by using readout lines connected to the respective microelectrodes and a readout line connected to the comparison electrode; and means for optically measuring a state of the cell arranged on the transparent substrate.

(14) The myocardial toxicity examining device according to (13) above, wherein each of the cell holders ($CH_G$, $CH_n$) is defined as a space surrounded by non-cell-adherent walls on the transparent substrate and the wall have one or more gaps that do not allow the cell to pass therethrough.

(15) The myocardial toxicity examining device according to (13) above comprising a barrier between the myocardial cell population-retaining region and the region in which the cell communication channel is formed, for blocking the flow of the cell culture solution, where the barrier is provided with an opening that allows cooperation between a cell retained in one of the plurality of the cell holders ($CH_G$) in the myocardial cell population-retaining region and a cell in the cell holder ($CH_n$) at the end of the cell communication channel.

(16) A myocardial toxicity examining device comprising:
a transparent substrate;
a myocardial cell population-retaining region comprising a plurality of cell holders ($CH_G$) arranged on the transparent substrate;
a cell communication channel comprising a tandemly-arranged plurality of cell holders ($CH_n$) each retaining a myocardial or fibroblast cell which conduct pulse from the myocardial cell population in cooperation with one of the cells of the cell holders ($CH_G$) in the myocardial cell population-retaining region;
a region for filling a cell culture solution therein, defined by the surface of the transparent substrate and walls formed around the myocardial cell population-retaining region and the cell communication channel;
means for feeding and draining the cell culture solution into and from the region surrounded by the walls;
means for adding a drug that acts on the cells to the cell culture solution;
a microelectrode provided on the transparent substrate and having thereon a myocardial cell in one of the cell holders ($CH_G$) in the myocardial cell population-retaining region;
a plurality of microelectrodes provided on the transparent substrate and having thereon a myocardial or fibroblast cell in each of the plurality of the cell holders (CHO in the cell communication channel;
a comparison electrode provided within the region surrounded by the walls;

means for measuring and recording potentials of the cells on the microelectrodes by using readout lines connected to the respective microelectrodes and a readout line connected to the comparison electrode;
a stage for supporting the transparent substrate, which can be driven in the X-Y directions; and
means for optically measuring a state of the cell arranged on the transparent substrate supported by the stage.

(17) A myocardial toxicity examining chip comprising:
a transparent substrate;
a myocardial cell population-retaining region comprising a plurality of cell holders ($CH_G$) provided on the transparent substrate for retaining myocardial cells;
a cell communication channel comprising a tandemly-arranged plurality of cell holders ($CH_n$) each retaining a myocardial or fibroblast cell, which conduct pulse from the myocardial cell population in cooperation with one of the cells of the cell population;
a region for filling a cell culture solution therein, defined by the surface of the transparent substrate and walls formed around the myocardial cell population-retaining region and the cell communication channel;
a microelectrode provided on the transparent substrate and having thereon a myocardial cell in one of the cell holders ($CH_G$) in the myocardial cell population-retaining region;
a plurality of microelectrodes provided on the transparent substrate and each having thereon a myocardial or fibroblast cell in each of the plurality of the cell holders ($CH_n$) in the cell communication channel;
a comparison electrode provided within the region surrounded by the walls; and
readout lines connected to the respective microelectrodes and a readout line connected to the comparison electrode.

(18) A method for examining myocardial toxicity using the myocardial toxicity examining device according to any one of (13)-(16) above, comprising the step of evaluating whether or not addition of a drug that acts on the cells to a cell culture solution delays the rate of the pulse generated by the myocardial cell population to propagate through the cell communication channel, thereby examining toxicity of the drug that acts on the cell on cardiac muscle.

(19) A myocardial toxicity examining device comprising:
a transparent substrate;
a cell population comprising a circularly arranged plurality of stably-pulsating myocardial cells on the transparent substrate;
walls formed on the transparent substrate for filling around the cell population and the cell communication channel with a cell culture solution;
means for feeding and draining the cell culture solution into and from the region surrounded by the walls;
means for adding a drug that acts on the cells to the cell culture solution;
a microelectrode provided on the transparent substrate and having thereon one of the cells of the cell population;
a plurality of separate microelectrodes provided on the transparent substrate and having thereon some of the cells of the cell communication channel;
a comparison electrode provided within the region surrounded by the walls;
means for measuring and recording potentials of the cells on the microelectrodes by using readout lines connected to the respective microelectrodes and a readout line connected to the comparison electrode;
means for applying electrical stimulation that excites the cell placed on the microelectrode to pulsate by using the readout lines connected to the respective microelectrodes and the readout line connected to the comparison electrode; and means for optically measuring a state of one of the cells arranged on the transparent substrate.

(20) A myocardial toxicity examining device comprising:
a transparent substrate;
a cell population comprising a circularly arranged plurality of stably-pulsating myocardial cells on the transparent substrate;
walls formed on the transparent substrate for filling around the cell population and the cell communication channel with a cell culture solution;
means for feeding and draining the cell culture solution into and from the region surrounded by the walls;
means for adding a drug that acts on the cells to the cell culture solution;
a microelectrode provided on the transparent substrate and having thereon one of the cells of the cell population;
a plurality of separate microelectrodes provided on the transparent substrate and having thereon some of the cells of the cell communication channel;
a comparison electrode provided within the region surrounded by the walls;
means for measuring and recording potentials of the cells on the microelectrodes by using readout lines connected to the respective microelectrodes and a readout line connected to the comparison electrode;
electrical stimulation means using a movable microelectrode for applying electrical stimulation that excites a certain cell or cell population among the cells placed on the microelectrodes to pulsates; and
means for optically measuring a state of one of the cells arranged on the transparent substrate.

(21) A myocardial toxicity examining device comprising:
a transparent substrate;
a cell population comprising a circularly arranged plurality of stably-pulsating myocardial cells on the transparent substrate;
walls formed on the transparent substrate for filling around the cell population and the cell communication channel with a cell culture solution;
means for feeding and draining the cell culture solution into and from the region surrounded by the walls;
means for adding a drug that acts on the cells to the cell culture solution;
a comparison electrode provided within the region surrounded by the walls;
electrical stimulation means using a movable microelectrode for applying electrical stimulation that excites a certain cell or cell population among the circularly arranged cells to pulsate;
means for measuring and recording a potential of the certain cell or cell population among the circularly arranged cells with the movable microelectrode; and
means for optically measuring a state of one of the cells arranged on the transparent substrate.

(22) A myocardial toxicity examining device comprising:
a transparent substrate;
a cell population comprising a circularly arranged plurality of stably-pulsating myocardial cells on the transparent substrate;
walls formed on the transparent substrate for filling around the cell population and the cell communication channel with a cell culture solution;
means for feeding and draining the cell culture solution into and from the region surrounded by the walls;

means for adding a drug that acts on the cells to the cell culture solution;
a ring-shaped microelectrode provided on the transparent substrate and having the same shape as the circularly-arranged cell population;
a comparison electrode arranged to surround the microelectrode;
means for measuring and recording potentials of the cells on the microelectrodes by using readout lines connected to the respective microelectrodes and a readout line connected to the comparison electrode;
electrical stimulation means using a movable microelectrode for applying electrical stimulation that excites a certain cell or cell population among the cells placed on the microelectrodes to pulsate; and
means for optically measuring a state of one of the cells arranged on the transparent substrate.

(23) A myocardial toxicity examining device, comprising:
a photo-sensitive-element array substrate obtained by removing a photoelectric conversion surface from a photosensitive element of a camera so as to directly measure an electric signal;
a cell population comprising a circularly arranged plurality of stably-pulsating myocardial cells on the photo-sensitive-element array substrate;
walls formed on the photo-sensitive-element array substrate for filling around the cell population and the cell communication channel with a cell culture solution;
means for feeding and draining the cell culture solution into and from the region surrounded by the walls;
means for adding a drug that acts on the cells to the cell culture solution;
a comparison electrode arranged to surround the photo-sensitive-element array substrate;
means for measuring and recording potentials of the cells on each photo-sensitive element on the photo-sensitive-element array substrate; and
electrical stimulation means using a movable microelectrode for applying electrical stimulation that excites a certain cell or cell population among the cells placed on the photo-sensitive element to pulsate.

(24) A method for examining myocardial toxicity by using the myocardial toxicity examining device according to any one of (19)-(23) above, comprising the step of evaluating whether or not addition of a drug that acts on the cells to a cell culture solution delays the rate of the pulse generated by the myocardial cell population to propagate through the cell communication channel, thereby examining toxicity of the drug that acts on the cell on cardiac muscle.

(25) The method for examining myocardial toxicity according to any one of (12), (18) and (24) above, comprising the step of quantitatively comparing the difference in pulse data between successive pulses of a certain cell to evaluate whether or not the fluctuation in that difference exceeds a certain value, thereby evaluating toxicity of a drug that acts on the cell on cardiac muscle.

(26) The method for examining myocardial toxicity according to any one of (12), (18) and (24), wherein the cells are arranged in the circular cell network so as to obtain cell arrangement that allows selection among multiple conduction pathways, the method comprising the step of judging whether or not the conduction pathways differ among rounds, thereby evaluating toxicity of a drug that acts on the cell on cardiac muscle.

According to the present invention, each cell is confined to a particular spatial configuration to form a population of myocardial cells having appropriately controlled sizes for use as a stably pulsating pacemaker. Then, a pulsating cell communication channel in which a plurality of myocardial cells and fibroblast cells are tandemly arranged is formed to interact with said cell population. Pulse generated by the myocardial cell population in the presence of a general culture solution is propagated through the pulsating cell communication channel to the tandemly-arranged myocardial cells and fibroblast cells. The state of this propagation is measured in terms of cell potentials of an electrode provided for one myocardial cell of the myocardial cell population and electrodes provided for some of the tandemly-arranged myocardial cells and fibroblast cells. Moreover, the pulsating states of the myocardial cells of the tandemly-arranged pulsating cells are optically detected.

Subsequently, the same measurement and detection are carried out in the presence of a culture solution containing a drug that acts on myocardial cells, thereby evaluating toxicity of the drug on the myocardial cells by comparing the results of the measurements and detections.

Effect of the Invention

Propagation of pulse for each of myocardial cells and fibroblast cells can be accurately measured and evaluated as cell potentials and optical data.

BRIEF DESCRIPTION OF THE DRAWINGS

The file of this patent contains at least one drawing executed in color. Copies of this patent with color drawings(s) will be provided by the Patent and Trademark Office upon request and payment of the necessary fee.

FIGS. 4(a), 4(b) and 4(c) are diagrams showing signals associated with measurement of cell potentials. Each diagram shows time along the horizontal axis and the cell potential between the microelectrode 2 and the comparison electrode $2_C$ along the vertical axis.

FIGS. 5(a), 5(b) and 5(c) are diagrams showing signals associated with the changes in the volume due to cell pulsation, which is measured with the optical system.

FIG. 6(a) shows changes in the potentials according to the amounts of $Na^+$, $Ca^{2+}$ and $K^+$ ion influx/efflux into/from the target cells under a normal state where the culture solution is free of drug. FIG. 6(b) shows changes in the potentials according to the amounts of $Na^+$, $Ca^{2+}$ and $K^+$ ion influx/efflux into/from the target cells under a state where the culture solution contains a drug.

FIG. 9(a) shows an exemplary change in the cell potentials upon addition of a drug; and FIG. 9(b) shows one example of Poincare plots for evaluating homology between two successive pulses with respect to the change in the cell potentials upon each pulsation.

FIG. 10(a) is a schematic view showing an exemplary re-entry circuit prepared with a circular network of myocardial cells by means of a cell arrangement technique at single-cell level; and FIG. 10(b) is a microscopic picture showing an actual exemplary arrangement of the cells on the microelectrodes.

FIG. 11(a) is a schematic view showing an exemplary re-entry circuit prepared with a circular network of myocardial cells with a cell population at certain spaced intervals; FIG. 11(b) is a microscopic picture showing an actual exemplary arrangement of the cells on the microelectrodes; and FIG. 11(c) is a microscopic picture showing an actual exemplary circular arrangement of the cell population on the microelectrode array.

FIG. 12(a) is a schematic view showing an exemplary re-entry circuit measurement device using a circular electrode; and FIG. 12(b) is a graph showing normal pulse data and abnormal pulse data actually measured with the electrode.

FIG. 13(a) is a schematic view showing an exemplary arrangement of an electrode for measuring potentials of a single cell and the cell; FIG. 13(b) shows a picture of the isolated single cell on the electrode actually measured with the electrode and electric pulse data thereof; and FIG. 13(c) shows a picture of a cell population measured on the electrode and a graph showing electric pulse data of one of the cells of the cell population.

FIG. 16 is a schematic view for illustrating cardiac information that can be measured with a cell measurement system of the present invention.

EMBODIMENTS FOR CARRYING OUT THE INVENTION

Figure 1:
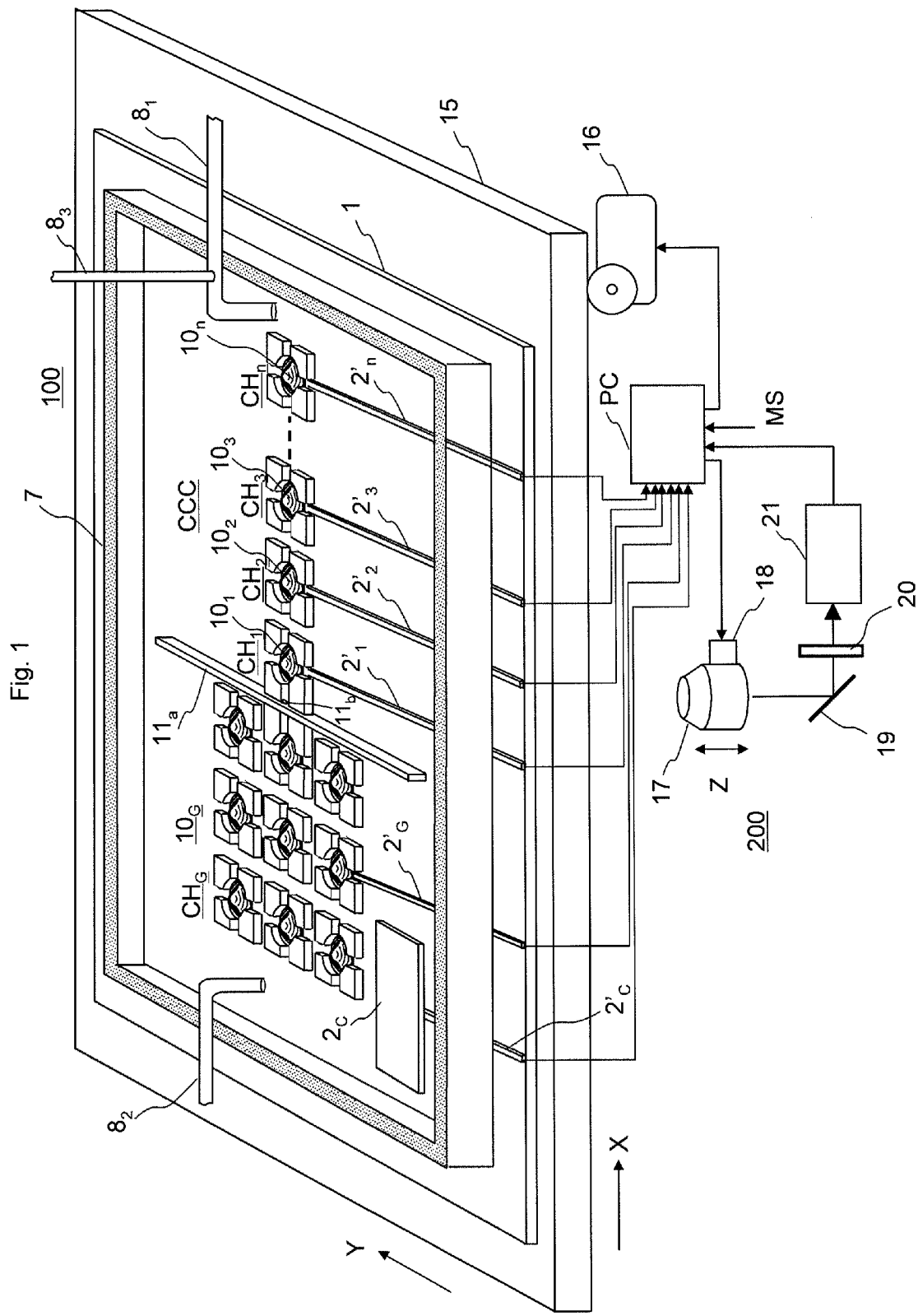
FIG. 1 is a perspective view schematically showing an exemplary structure of a myocardial toxicity examining device according to an example of the present invention.
Figure 2:
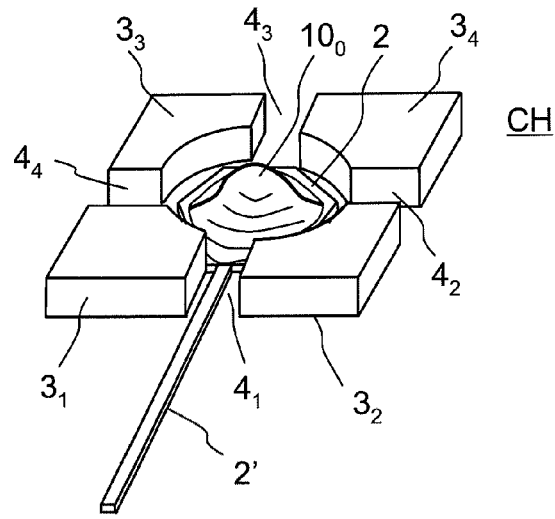
FIG. 2 is a perspective view schematically showing an exemplary structure of a cell holder CH of the myocardial toxicity examining device shown in FIG. 1.
Figure 3:
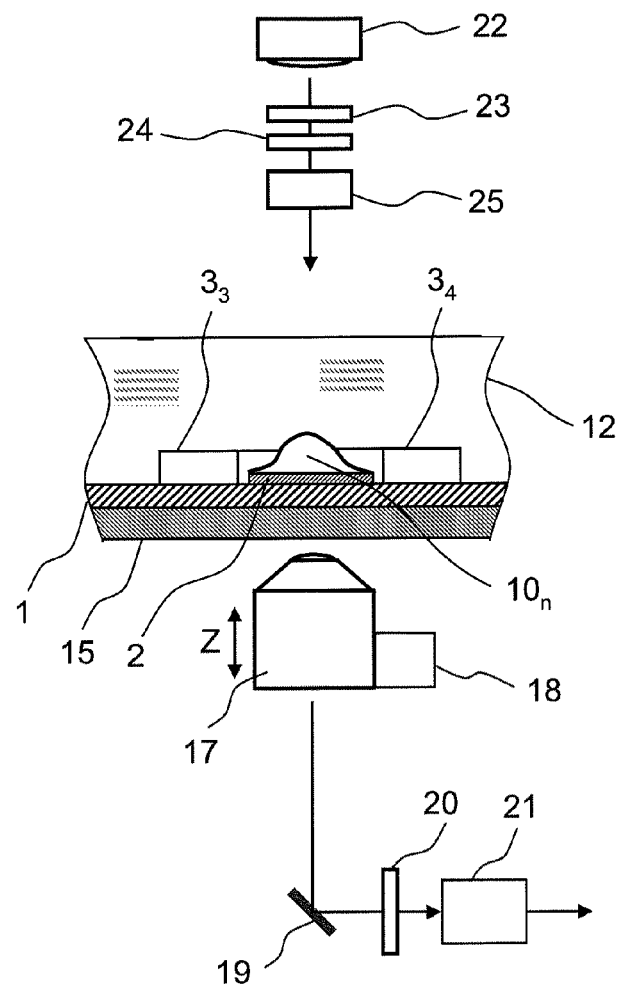
FIG. 3 is a diagram for illustrating an optical system for optically detecting a cell on the cell holder CH of the myocardial toxicity examining device shown in FIG. 1.

FIG. 1 is a perspective view schematically showing an exemplary structure of a device for examining myocardial toxicity according to an example of the present invention. FIG. 2 is a perspective view schematically showing an exemplary structure of a cell holder CH of the myocardial toxicity examining device shown in FIG. 1. FIG. 3 is a view for illustrating an optical system for optically detecting the cell retained in the cell holder CH of the myocardial toxicity examining device shown in FIG. 1.

Reference numeral 100 denotes the myocardial toxicity examining device, which mainly consists of parts built on a transparent substrate 1. The transparent substrate 1 is an optically transparent material, for example, a glass substrate or a silicon substrate. Reference numerals 2 denote microelectrodes, for example, transparent ITO electrodes, arranged on the transparent substrate 1. Reference numerals 2' denote readout lines from the microelectrodes 2. Reference numerals $3_1$, $3_2$, $3_3$ and $3_4$ are agarose gel walls, which are arranged around each of the microelectrode 2 with gaps $4_1$, $4_2$, $4_3$ and $4_4$. The agarose gel walls $3_1$, $3_2$, $3_3$ and $3_4$ are cutout in the middle to form a space as a cell housing. The microelectrode 2 is placed on the transparent substrate 1, as necessary, within the space as the cell housing formed with the agarose gel walls $3_1$, $3_2$, $3_3$ and $3_4$. Regardless of the presence of the microelectrode 2, a single cell 10 can be retained in the cell housing. In FIG. 2, the microelectrode 2 is arranged on the transparent substrate 1 within the space as the cell housing formed with the agarose gel walls $3_1$, $3_2$, $3_3$ and $3_4$, where a myocardial cell $10_0$ is retained as well on the microelectrode 2. The microelectrode 2 is shown to be connected to the readout line 2'. A material, e.g., collagen, which helps a cell to adhere to the electrode surface or the transparent substrate, is preferably applied onto the cell-bearing surface of the microelectrode 2 or, when the cell is placed without the microelectrode 2, directly onto the transparent substrate 1. Since the cell within the cell housing formed with the agarose gel walls $3_1$, $3_2$, $3_3$ and $3_4$ is non-adherent to the agarose gel, the cell 10 will not transfer beyond the walls even if its height is equivalent to the heights of these walls $3_1$, $3_2$, $3_3$ and $3_4$. Furthermore, since the gaps $4_1$, $4_2$, $4_3$ and $4_4$ surrounding the cell housing formed by cutting out in the middle of the agarose gel walls $3_1$, $3_2$, $3_3$ and $3_4$ are smaller than the size of the cell, the cell 10 will not transfer by passing through these gaps $4_1$, $4_2$, $4_3$ and $4_4$.

With reference to FIG. 1, the cell holders $CH_1$, $CH_2$, $CH_3$ and $CH_n$ each retains a myocardial cell or a fibroblast cell $10_1$, $10_2$, $10_3$ or $10_n$ in the cell housing. Each holder is provided, although not evident from the figure, with the microelectrode 2 from which extends the readout line $2'_1$, $2'_2$, $2'_3$ or $2'_n$. These myocardial cells or fibroblast cells form a tandemly arranged cell communication channel CCC. Here, "n" is, for example, 20. Although these twenty tandemly-arranged myocardial and fibroblast cells may be allocated randomly, the cells in the cell holders $CH_1$ and $CH_{20}$ are preferably myocardial cells. On the left side of this cell communication channel CCC are provided 3×3 cell holders $CH_G$ to form a region that retains a myocardial cell population $10_G$ where each cell holder CH retains a myocardial cell 10. This cell population $10_G$ serves as a stably-pulsating pacemaker. Among the cell population $10_G$, only one of the cell holders CH is provided with the microelectrode 2 from which extends a readout line $2'_G$. In addition, the right middle cell holder CH of the cell population $10_G$ is arranged to face the cell holder $CH_1$ of the cell communication channel CCC. A barrier $11_a$ is provided on the right of the cell population $10_G$ and the left of the cell communication channel CCC. A small opening $11_b$ is formed in the lower middle part of this barrier $11_a$. On both sides of this opening $11_b$, the right middle cell holder CH of the cell population $10_G$ is facing the cell holder $CH_1$ of the cell communication channel CCC so as to allow physical contact/intercellular interaction between the cells retained in the cell housings via the gaps 4 at the periphery of the housings. A comparison electrode $2_C$ is provided below the cell population $10_G$, from which a readout line $2'_C$ extends.

Reference numeral 7 denotes a surrounding wall that surrounds the cell population $10_G$, the cell communication channel CCC and the comparison electrode $2_C$. Reference numerals $8_1$ and $8_2$ denote pipes for supplying a cell culture solution into the region surrounded by the wall 7 and for draining the cell culture solution from the region surrounded by the wall 7. In the case of this figure, a culture solution is supplied from the pipe $8_1$ extending toward the bottom surface of the substrate 1 and drained from the pipe $8_2$ extending from the bottom surface of the substrate 1. A pipe $8_3$ is connected to the culture solution-supplying pipe $8_1$ near the culture solution outlet so that a drug that acts on the cells is supplied via this pipe $8_3$. Accordingly, the cells 10 are exposed to the cell culture solution supplied from the pipe $8_1$ into the region surrounded by the wall 7, while being stably retained on the microelectrodes 2. Once the cells no longer need to be exposed to the culture solution, the culture solution can be drained from the region surrounded by the wall 7 with the pipe $8_2$. Moreover, when the culture solution needs to be exchanged with a fresh culture solution, the culture solution may be supplied after or while draining the cell culture solution. On the other hand, if one wants to affect the cells with a drug, the drug for affecting the cells may be added to the culture solution via the pipe $8_3$ so as to be supplied together with the culture solution via the pipe $8_1$ while draining the cell culture solution from the pipe $8_2$. In this case, due to the barrier $11_a$ provided between the cell population $10_G$ and the cell communication channel CCC, when the culture solution containing the drug is supplied into the region surrounded by the wall 7 from the pipe $8_1$, the cells of the cell population $10_G$ are less influenced by the drug than the cells of the cell communication channel CCC. Specifically, when a drug-containing culture solution is supplied via the pipe $8_1$, this culture solution flows through the spacings between the wall 7 and the both edges of the barrier $11_a$ as well as over the top of the barrier $11_a$ toward the cell population $10_G$. Thus, the cells of the cell population $10_G$ are also affected by the drug. This influence, however, is indirect compared to the influence on the cells of the cell communication channel CCC, and thus it does not affect the function as a pacemaker. The structures and arrangements of the pipes $8_1$, $8_2$ and $8_3$ may arbitrarily be changed depending on the measurement configuration. For example, the pipes $8_1$ and $8_3$ may be separated, or the pipe $8_2$ may be omitted while using the pipe $8_1$ for both supply and drainage.

PC refers to a personal computer, which measures and records the cell potentials between the readout lines 2' from the microelectrodes 2 of the cell holders CH and the readout line 2' from the comparison electrode $2_C$. Furthermore, operation signals Ms from an operator are input into the personal computer PC.

The myocardial toxicity examining device 100 may be mounted on an XY stage 15 of the optical observation device 200 where the pulsation of a certain cell 10 of the cell communication channel CCC can be observed with an optical system. The XY stage 15 is optically transparent and may be moved to a certain positions with an X-Y driver 16 according to the signal given by the personal computer PC reflecting the operation signal Ms from the operator. FIG. 3 shows an exemplary configuration for observing the pulsating state of cell $10_n$ of the cell communication channel CCC. Reference numeral 12 denotes a culture solution.

Reference numeral 22 denotes light source of a phase-contrast microscope or a differential interference microscope. Generally, a halogen lamp is used. Reference numeral 23 denotes a bandpass filter that only passes light with a specific wavelength from the light source for observation with a stereoscopic microscope such as a phase-contrast microscope. For example, in the case of observing the cell $10_n$, narrow-band light having a wavelength in the vicinity of 700 nm is used to prevent damage of the cell $10_n$. Reference numeral 24 denotes a shutter that has a function of blocking irradiation light while no image measurement is going on, for example, while moving the XY stage 15. Reference numeral 25 denotes a condenser lens, where a phase ring is installed for phase-contrast observation or a polarizer for differential interference observation. The cell response measurement device 100 formed on the substrate 1 is mounted on the XY stage 15 which can be moved with the X-Y driver 16 to observe and measure certain location of the cell response measurement device 100. The pulsating state of the cell $10_n$ in the cell response measurement device 100 is observed with an objective lens 17. The focal position of the objective lens 17 can be transferred in the Z-axis direction with a driver 18 according to the signal from the personal computer PC. The magnification of the objective lens 17 may be 40 or higher. The objective lens 17 allows observation of a phase-contrast image or a differential interference image of the cell $10_n$ obtained with light transmitted from the light source 22. A diachronic mirror 19 and a bandpass filter 20 that reflect light having the same wavelength as the light that passes through the bandpass filter 23 allow observation of only a phase-contrast microscope image or a differential interference microscope image with a camera 21. The image signal observed with the camera 21 is input into the personal computer PC.

Exemplary dimensions of the structures of the myocardial toxicity examining device 100 shown in FIG. 1 are as follows. In this example, the size of a cell is 10 $\mu m \phi$. The transparent substrate 1 has dimensions of 100 mm×150 mm, the microelectrode 2 has dimensions of 8 $\mu m \times 8$ $\mu m$ and each of the agarose gel walls $3_1$, $3_2$, $3_3$ and $3_4$ has dimensions of 20 $\mu m \times 20$ $\mu m \times 10$ $\mu m$ (height). Each of the gaps $4_1$, $4_2$, $4_3$ and $4_4$ has a width of 2 $\mu m$, the cell housing formed with the agarose gel walls $3_1$, $3_2$, $3_3$ and $3_4$ has a 12 $\mu m \phi$ cylindrical space, and the wall 7 has external dimensions of 5 mm×5 mm with a height of 5 mm. The height of the barrier $11_a$ is 1 mm. Although the microelectrode 2 has a square shape of 8 $\mu m \times 8$ $\mu m$ in this example, it may be a circular electrode of 10 $\mu m \phi$ that corresponds to the shape of the cell housing made with the agarose gel walls $3_1$, $3_2$, $3_3$ and $3_4$ and the widths of the gaps $4_1$, $4_2$, $4_3$ and $4_4$.

Hereinafter, an exemplary structure of the cell response measurement device 100 of the present invention and a specific example of measurement using the same will be described.

FIGS. 4(a), 4(b) and 4(c) are diagrams showing signals associated with measurement of cell potentials. Each diagram shows time along the horizontal axis and the cell potential between the microelectrode 2 and the comparison electrode $2_C$ along the vertical axis. FIG. 4(a) shows cell potentials resulting from the pulses of the cell population $10_G$. Here, a potential refers to one between the readout line $2'_G$ extending from one of the cell population $10_G$ and the readout line $2'_C$ extending from the comparison electrode $2_C$ shown in FIG. 1. The diagram shows stable pulses indicating that the cells are capable of serving as a pacemaker. FIG. 4(b) shows cell potentials resulting from the pulses of a target cell in a normal state where the culture solution does not contain a drug. Here, a cell targeted for measurement is the cell $10_n$ of the cell communication channel CCC, where the potential between the readout line $2'_n$ extending from the cell $10_n$ and the readout line $2'_C$ extending from the comparison electrode $2_C$ are measured. As can be appreciated from comparison with the waveform of FIG. 4(a), the time required for conducting pulse of the cell 10 of the cell communication channel CCC is delayed for $\Delta t$. Meanwhile, FIG. 4(c) shows cell potentials resulting from the pulse of the target cell in a state where the culture solution contains a drug. Again, the cell targeted for measurement is the cell $10_n$ of the cell communication channel CCC for the sake of facilitating comparison with FIG. 4(b). As can be appreciated from comparison with the waveforms of FIGS. 4(a) and 4(b), the time required for conducting pulse of the cell 10 of the cell communication channel CCC is found to be delayed not just for $\Delta t$ but for $\Delta t+\alpha$. This means that the level of the Na-ion inhibition due to the drug acting on the cell of the cell communication channel CCC appears as the increase in the delayed time, i.e., $+\alpha$. Specifically, toxicity of a drug on a myocardial cell can be assessed as Na-ion inhibition.

FIGS. 5(a), 5(b) and 5(c) are diagrams showing signals associated with the changes in the volume due to pulse of cells, which is measured with the optical system. FIG. 5(a) shows the change in the volume associated with pulse of a cell of cell population $10_G$, where pulse of one of the cells of the cell population $10_G$ is optically detected with the configuration shown in FIG. 3. The contraction and dilatation associated with the pulsation of the cell can be observed as pulse-shaped changes. The cycle of this waveform is the same as the cycle of the changes in the cell potential associated with the pulsation shown in FIG. 4(a). FIG. 5(b) shows, in the upper diagram, the change in the volume associated with the pulsation of the target cell under the normal state where the culture solution is free of the drug, and shows, in the lower diagram, a waveform of the same in time-differential values for evaluation as electric signals. Again, the cell targeted for measurement is the cell $10_n$ of the cell communication channel CCC, where the pulse of the cell $10_n$ is optically detected with the configuration shown in FIG. 3. As can be appreciated from comparison with the waveform shown in FIG. 5(a), the time required for conducting pulse of the cell 10 of the cell communication channel CCC is delayed for $\Delta t$. Meanwhile, FIG. 5(c) shows diagrams for evaluating changes in the volume associated with the pulsation of the target cell under the state where the culture solution contains a drug. In FIG. 5(c), the time axes are stretched out as compared to those in FIGS. 5(a) and 5(b). The upper diagram represents a waveform corresponding to the waveform of the upper diagram of FIG. 5(b), where the time required for conducting pulse of the cell 10 of the cell communication channel CCC is further delayed for $\beta$ in addition to $\Delta t$ as can be appreciated by comparison with the waveform shown in FIG. 5(a). The influence on the change in the volume associated with the pulsation of the target cell is more prominent in smaller inclination of the change in the volume rather than the increase in the delay. This is apparent from comparison with the change in the volume with a drug-free culture solution shown as a reference waveform in the lower diagram in FIG. 5(c). The middle diagram of FIG. 5(c) shows the waveform of the upper diagram processed as time-differential values for evaluation thereof. As can be appreciated by comparing the time-differential values with those shown in the lower diagram of FIG. 5(b), the smaller the peak value becomes, the smoother the inclination becomes. This means that the drug decreased the contraction rate of cardiac muscle and therefore the cardiac output is also decreased. In other words, toxicity of a drug on the myocardial cell can be evaluated as decrease in the contraction rate.

FIG. 6(a) shows changes in the potentials according to the amounts of $Na^+$, $Ca^{2+}$ and $K^+$ ion influx/efflux into/from the target cells under a normal state where the culture solution is free of drug. FIG. 6(b) shows changes in the potentials according to the amounts of $Na^+$, $Ca^{2+}$ and $K^+$ ion influx/efflux into/from the target cells under a state where the culture solution contains a drug. As can be appreciated by a glance of comparison between FIGS. 6(a) and 6(b), QT delay emerges where the waveform is stretched along the time axis. Moreover, the waveform is largely deformed due to influx/efflux of the $K^+$ ion. In order to evaluate this as electric signals, durations of the detected 30%, 60% and 90% values are shown as APD30, APD60 and APD90, respectively, with respect to the broken lines indicating the values between "0" and "100" in the diagram. Here, APD stands for Action Potential Duration. Evaluations of the magnitudes and percentages of these values can provide evaluation of influence of the drug on the amounts of the $Na^+$, $Ca^{2+}$ and $K^+$ ion influx/efflux.

Figure 7:
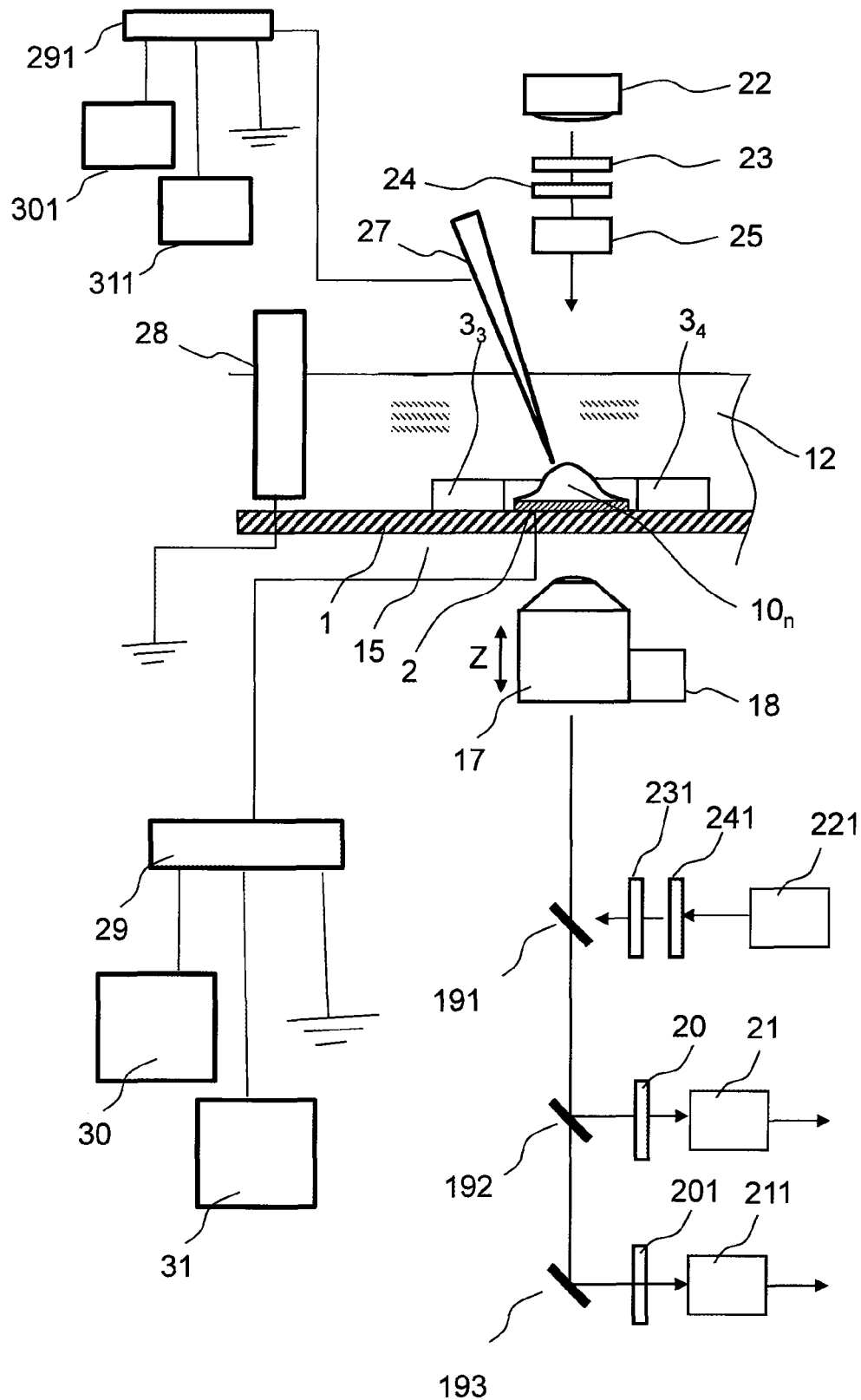
FIG. 7 is a view for illustrating an exemplary arrangement of an optical system and a movable electrode of the myocardial toxicity examining device for optically detecting the cells.

FIG. 7 is a view for illustrating an exemplary arrangement of an optical system and a movable electrode of the myocardial toxicity examining device for optically detecting the cells, in which observation of the pulsating state, for example, of the cell $10_n$ to be measured is exemplified. Reference numeral 12 denotes a culture solution. Reference numeral 22 denotes light source for a phase-contrast microscope or a differential interference microscope, which is generally a halogen lamp. Reference numeral 221 denotes fluorescent light source for fluorescent measurement of the cells, which is generally a mercury lamp, monochromatic laser, LED light source or the like. Reference numeral 23 denotes a bandpass filter that passes only light with a particular wavelength from the light source for observation with a stereoscopic microscope such as a phase-contrast microscope, while reference numeral 231 denotes a bandpass filter that passes only light with an excitation wavelength that excites particular fluorescence from the fluorescent light source 221. For example, in the case of observing the change in the shape such as information of change in the volume of the pulse of the cell $10_n$, an image that passed the bandpass filter 20 that allows only light with a wavelength for measuring the cell shape is measured with the camera 21 on a real-time basis, where narrowband light having the wavelength in the vicinity of 700 nm is used for measurement to prevent damage of the cell $10_n$. Reference numerals 24 and 241 denote shutters that have a function of blocking irradiation light while no image measurement is going on, for example, while moving the XY stage 15. Reference numeral 25 denotes a condenser lens, where a phase ring is installed for phase-contrast observation or a polarizer for differential interference observation. In the case of fluorescent measurement, for example, in the case of intracellular calcium release measurement, a combination of a bandpass filter that selectively passes light with the excitation wavelength of approximately 500 nm and a bandpass filter that selectively passes light with the fluorescent measurement wavelength of approximately 600 nm is used, to measure, with the camera 211, the fluorescent image that passed through the bandpass filter 201 that only selectively passes light with the fluorescent wavelength. In this case, if calcium release per cell unit in the cell network is to be measured in terms of time to determine the pathway of the signal conduction in the cell network, continuous high-speed images can be acquired with the time resolution of the camera being 0.1 ms or less. The cell response measurement device 100 formed on the substrate 1 is mounted on the XY stage 15 which can be moved with the X-Y driver 16 to observe and measure certain location of the cell response measurement device 100. The pulsating state of the cell $10_n$ in the cell response measurement device 100 is observed with an objective lens 17. The focal position of the objective lens 17 can be transferred in the Z-axis direction with a driver 18 according to the signal from the personal computer PC. The magnification of the objective lens 17 may be 40 or higher. The objective lens 17 allows observation of a phase-contrast image or a differential interference image of the cell $10_n$ obtained with light transmitted from the light source 22. A diachronic minor 192 and a bandpass filter 20 that reflect light with the same wavelength as the light that passes through the bandpass filter 23 allow observation of only a phase-contrast microscope image or a differential interference microscope image with a camera 21. The image signal observed with the camera 21 is input into the personal computer PC. Moreover, according to this example, a movable electrode 27 for stimulating a cell is arranged with a position controlling mechanism for adjusting the coordinates of the movable electrode with respect to not only over the plane parallel to the plane of the XY stage but also with respect to its height. Using this position controlling mechanism, the tip of the movable electrode is transferred to one or more particular cells in the cell network for stimulating them. The movable electrode may be a metal electrode provided with insulating coating except for the tip, a glass electrode having the opening size of the tip of about 5 micrometers or less, or the like, where any electrode that can apply electrical stimulation only to a particular cell or cells in the vicinity of the tip of the movable electrode can be used. When a metal electrode is used, platinum black or the like may be applied to the tip surface for effectively transmitting electrical stimulation to the cell(s). The positioning of the tip of the movable electrode can be adjusted according to the level of the response of the cell(s) to the electrical stimulation, and may make a contact with the cell(s) or placed near the cell(s). In addition, in order to accurately apply stimulation from the stimulation electrode to the target cell(s), the electrode 2 for measuring the cell potentials may be used as a ground electrode by switching the electrode at the moment of applying electrical stimulation, or a separate ground electrode 28 may be provided. Moreover, in order to stimulate a particular cell, the existing microelectrode 2 may be used as a stimulation electrode. In this case, the switching circuit 29 connected to the microelectrode is switched upon stimulation so that the microelectrode that is usually connected to an electric signal measurement circuit 30 is connected to an electrical stimulation circuit 31 for applying square-wave stimulation signals to the microelectrode 2. Furthermore, when the movable electrode 27 is used to provide stimulation, the switching circuit 29 may be switched to grounding state. On the other hand, the movable electrode may also be used not only as a stimulation electrode, but also as an electrode for measuring the electric signal of the cell(s) or as a ground electrode. In this case, the movable electrode is connected to a switching circuit 291, and switched, according to its use, i.e., for cell potential measurement, for cell stimulation or as a ground electrode, to be connected to an electric signal measurement circuit 301 to measure the cell potential, to be connected to an electrical stimulation circuit 311 for applying a square-wave stimulation signal to the cell(s) or to be grounded for use as a ground electrode, respectively. The timings of the electrical stimulation applied to the cells with the electrical stimulation circuits 31 and 311 can be employed primarily for the following two applications. One is to apply irregular stimulations between the pulse intervals of the normal myocardial cell network with an autonomous pulsation ability. The other is to provide pulse interval to the myocardial cell network with no autonomous pulsation ability. In both cases, changes in the response of the cell network can be traced through measurement by gradually shortening the cycle of the pulse interval (time interval between two pulses) by 5 ms. In order to do so, the electrical stimulation circuits 31 and 311 can analyze the pulsation cycle information acquired with the electric signal measurement circuits 30 and 301 and conduct feedback regulation based on the acquired results to determine the timing of the stimulation. Moreover, when the movable electrode 27 is used for the electric signal measurement, measurement can equivalently be carried out in the present system without the microelectrode 2. Since the pulsation cycle of each cell in the cell network can be measured by the optical measurement installed in the system, a change from a stable state to an unstable state such as abnormal cardiac rhythm in this pulsation cycle can be measured only with the optical measurement device arranged in the system. Then, if necessary, the movable electrode is used to acquire the data of the electric property of the particular cell from these results. In this case, the number of the microelectrodes arranged on the system in the first place is not limited, and a larger cell network can be configured freely as long as optical measurement is possible.

Figure 8:
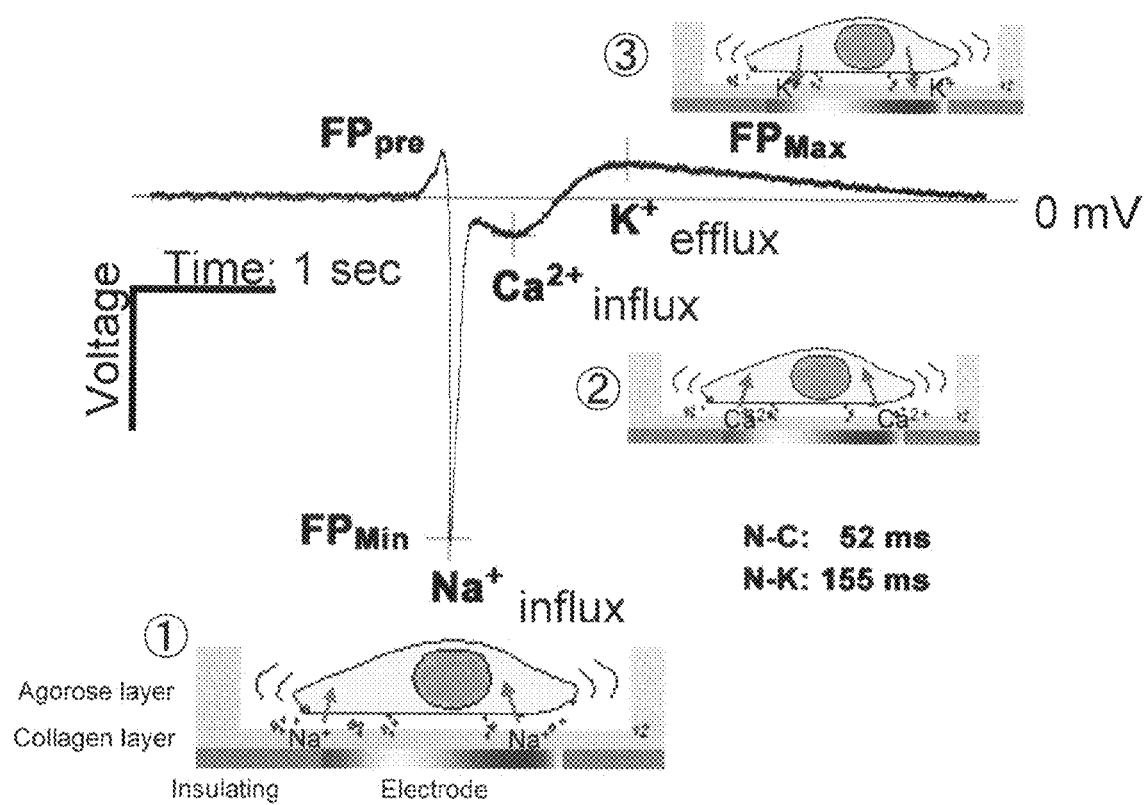
FIG. 8 is a schematic view for illustrating generation of an electric signal of a cell.

FIG. 8 shows a schematic view of an example of generation of an electric signal of a cell. First, influx of sodium ions into a cell occurs via sodium-ion channels in the cellular membrane, where the cell potential is rapidly decreased. Then, the cell potential is decreased after a slight delay due to influx of calcium ions, and then as the subsequent step, efflux of potassium ions from the cell occurs where the cell potential is increased. The changes in the cell potentials occur due to the different response properties of various ion channels present in the myocardial cellular membrane. By analyzing the positions of the peaks of change in the potentials caused by the respective ion channels as time characteristic of the ion channels, the changes in the waveforms of the electric signals can be measured for each type of the ion channels that are blocked due to the effect of the drug. As a result, inhibition effect of the drug on the ion channels can be estimated. There are four particularly important ion channels for evaluation of a drug, i.e., FastNa, SlowNa, Ca, IKr and IKs. Blockings of these four types of ion channels can be measured.

FIG. 9(a) shows influence on the electric signals of the cell shown in FIG. 8 upon actual addition of reagent E-4031 at various concentrations that selectively inhibits the potassium-ion channels. Since the IKr-ion channel that is responsible for efflux of K-ion from the cells and that increases the cell potential is inhibited, change in the cell potentials can be observed to be gradually delayed in the positive direction as the concentration of the drug increases. FIG. 9(a) shows data of a particular single pulsation of cellular response. In practice, the magnitude of the fluctuation width of the responses between the successive pulses is an important index for estimating the influence of the drug. FIG. 9(b) shows one example of an analysis technique where successive pulse data called Poincare plots are compared correlatively. Here, X-axis represents plots of response time of a particular ion channel upon n-th pulse while Y-axis represents plots of response time of the same ion channel upon (n+1)-th pulse. Accordingly, if the properties of the successive pulses are the same, plots will be drawn along the Y=X line represented by the broken line in the graph. If there is a significant fluctuation in the responses between the successive pulses, plots observed will be placed distant from the Y=X line. In fact, in this example, although addition of 40 nM results in the delay of the response time as compared to the control without addition of the drug, homology between the successive pulses remains the same. At the same time, these plots reveal that addition of the drug up to 400 nM further delays the response time, and homology is no longer retained between the successive pulses, resulting in generation of an unstable pulsation cycle. This result agrees with the results of prolongation in the QT interval measurement representing cardiac toxicity. Generation of prolongation of QT interval can be estimated by using the Poincare plots as the index of increase in the fluctuations of the successive pulses in cell level. This phenomenon can be described as follows: when a particular ion channel is blocked with a drug, only a phenomenon of decrease in the ion efflux ability is observed where the degree of the blocking is small where the cell response is not yet unstable whereas when the degree of blocking becomes larger the number of ion channels functioning are extremely decreased and thus reproducibility of ion efflux ability becomes lower and fluctuation becomes larger for the same cell. Hence, the magnitude of this fluctuation can be used as an index of likelihood of generating prolongation of QT interval.

FIG. 10(a) is a schematic view showing an example of a drug for re-entry circuit with a circular network of myocardial cells using a cell arrangement technique at a single-cell level. A circular network produced with only myocardial cells is used as a normal network model. A pathologic model such as cardiac hypertrophy is realized by incorporating fibroblast cells into the cell network. The fibroblast cells present in the network will cause delay of the conduction velocity or attenuation of the conduction of the myocardial cell network, as a result of which, generation of premature contraction can be estimated. FIG. 10(b) is a microscopic picture showing an example of actual arrangement of myocardial cells on the microelectrodes. In fact, when the cells are arranged on the microelectrodes in cell units as shown in this picture, delay in the signal conduction between the adjacent myocardial cells can be measured. Since this conduction velocity depends on the magnitude of the first electric signal generated upon pulsation, data of delay in this signal conduction can be used as the inhibitory effect on the Na-ion channel.

FIG. 11(a) is a schematic view showing an exemplary re-entry circuit by a circular network of myocardial cells using a cell population at certain spaced intervals. In the circular cell network in cell units shown in FIG. 10, pulsation signals of the myocardial cells are uniquely transmitted, and the cells will transmit pulsation signals between the adjacent cells while maintaining the same property unless there are fluctuations in the pulses of the cells themselves as shown in FIG. 9. On the other hand, when the cells were arranged at certain spaced intervals to form a circular network as shown in FIG. 11, the cell population will have flexibility to have different conduction pathways for different pulses as represented by solid line 35, broken line 36 and dotted line 37. In particular, when large fluctuation occurs in the response property of each myocardial cell due to addition of a drug as described with reference to FIG. 9, the cells that are likely to response differ in each case as the stimulation signals go around the circular network, rendering the difference in the pathways significant. Since this is the same mechanism as the mechanism of premature contraction, i.e., a fatal cardiac status called spiral/re-entry, measurement of spiral/re-entry becomes possible by particularly using a circular network based on cell population having such spaced intervals. FIG. 11(b) is a microscopic picture showing an actual exemplary arrangement of the cell population on the microelectrodes, in which the cell population has myocardial cells for about 60% and fibroblast cells for about 40%. In fact, such arrangement increases fluctuations in the conduction velocity between adjacent electrodes between successive pulses. Since the increase in the fluctuation becomes significant particularly by the addition of the drug, generation of spiral/re-entry can be estimated according to the change in the fluctuation width of the conduction velocity between successive pulses. FIG. 11(c) is a microscopic picture showing another example of actual circular arrangement of the cell population on the microelectrode array. For actual measurement of spiral/re-entry, calcium spike firing in each cell of the cell population network can be estimated at single-cell level by using a high-speed fluorescent measurement camera shown in FIG. 7. As a result, actual analysis of the pathway taken by the signal conduction of the cells and actual analysis of the change in the pathways at each round can be realized.

FIG. 12(a) is a schematic view showing an exemplary re-entry circuit measurement device using a circular electrode. In this example, a circular electrode 38 with an electrode width of 50-100 micrometers is formed into a ring shape to have a diameter of 1-3 mm and arranged on each of the bottom surfaces of a 96-well plate 42. The bottom surface of the plate other than the electrode is coated with a non-cell-adhesive material such as agarose so that the cell population 41 is circularly placed only on the electrode surface. A reference electrode ring 39 is placed concentrically on this non-cell-adhesive coated region, and a flow passage 40 is provided for entrance and exit of a reagent. By using such electrode, abnormal pulsation of a myocardial cell can be simply and conveniently measured. FIG. 12(b) is a graph showing normal pulse data and abnormal pulse data actually measured with the electrode. Although a circular electrode is used in this example, a system for optically measuring abnormal pulsation which is equivalently effective as this circular electrode can be constructed by using the optical measurement system shown in FIG. 7. In this case, an electric signal to be measured can be acquired by allowing the moving electrode shown in FIG. 7 to make contact with the circular cell network.

FIG. 13(a) is a schematic view showing an exemplary arrangement of a cell and a microelectrode 2 for measuring potentials of a single cell, which illustrates a measurement technique in which a single cell targeted for measurement is arranged on the microelectrode 2 with a diameter of 10 to 50 micrometers. Again in this example, likewise in other examples, the area of the bottom surface other than the electrode is coated with a non-cell-adhesive material such as agarose such that the cell is retained on that place on the electrode. FIG. 13(b) is a picture of an isolated single cell on the electrode which was actually measured with the microelectrode 2, and electric pulse data thereof. Signals of the isolated single cell are unstable and pulses are largely fluctuated as shown in the graph. On the other hand, in FIG. 13(c), a single cell is placed on the microelectrode 2 like FIG. 13(b) but to form a cell population with other cells, thereby realizing stability of the pulsation cycle as can be appreciated from the pulsation signal graph. In an actual pulse measurement at single-cell level, the magnitude of fluctuation between successive pulses serves as an index as shown in FIG. 9. Therefore, as described in the present example, a measurement system is useful in which only a certain cell to be measured is placed on the microelectrode while other myocardial cells are not provided on the electrode so as to maintain stability of this certain cell. Accordingly, pulse data of a single cell can be acquired while realizing stability by providing cell population.

Figure 14:
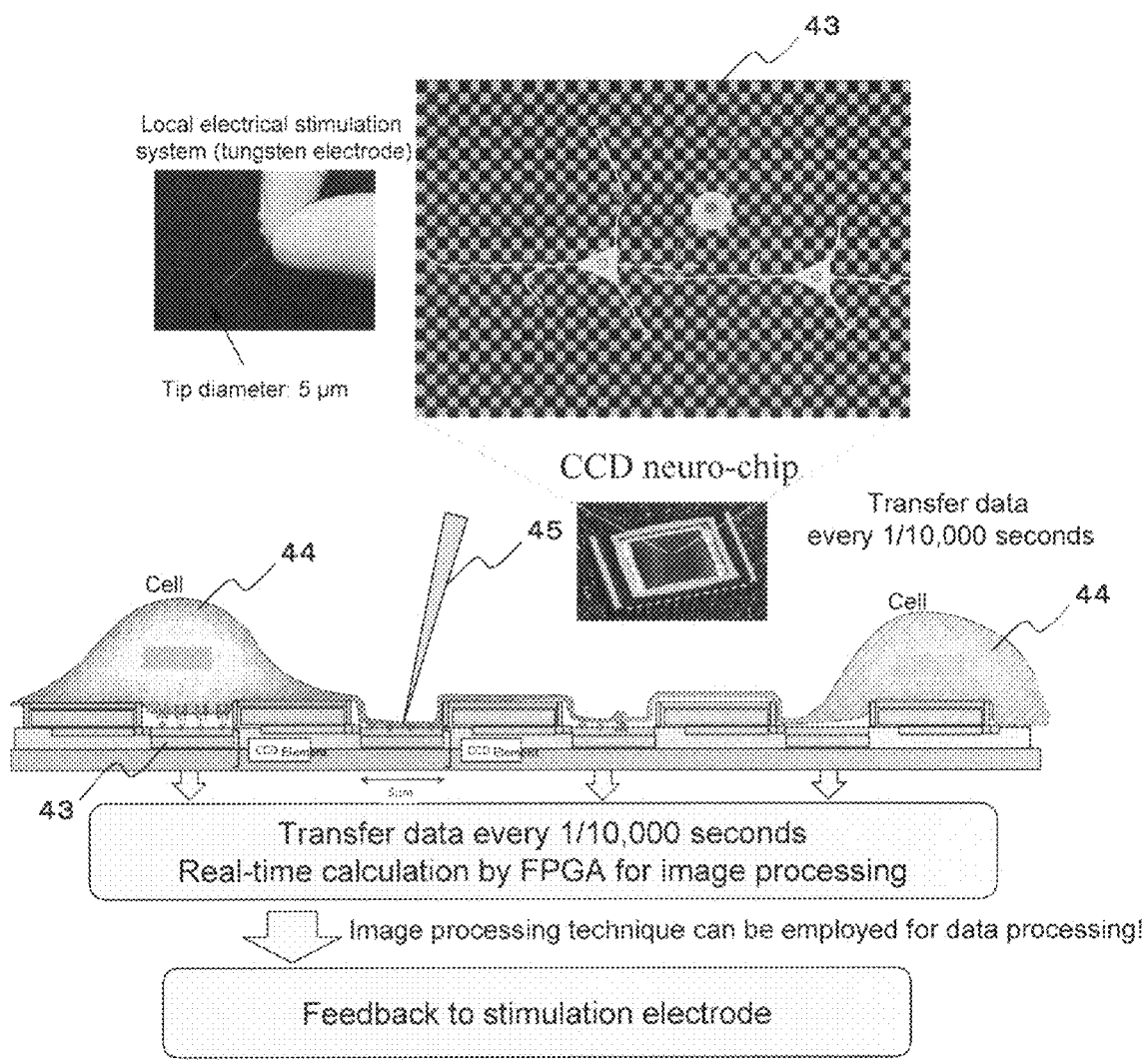
FIG. 14 is a schematic view for illustrating an example of the present invention in which a photo-sensitive element of the camera is used for measuring potentials of a single cell.

FIG. 14 is a schematic view for illustrating an example using a photo-sensitive element of the camera for measuring a potential of a single cell according to the present invention. In general, a photo-sensitive element of the camera converts a light signal into an electric signal on a photoelectric conversion surface to use this electric signal for measurement. This photoelectric conversion surface can be removed and an electric signal array can be used to obtain an electric signal in two dimensions. Therefore, since an electrode array at single-cell level can be used, for example, change in the signal conduction pathway in the cell population network with certain spaced intervals as shown in FIG. 11, i.e., generation of spiral/re-entry, can be measured, which requires simultaneous measurement of electric signals of respective cells in the cell population. In actual measurement, the intervals of measuring the pixels required are about $1/10,000$ seconds, and thus a photo-sensitive element of a high-speed camera with a shutter speed of $1/10,000$ seconds needs to be used. In this case, an image processing technique employed in conventional cameras can directly be applied to the acquired signal data of the cells, which allows real-time processing using FPGA for image processing. In addition, feedback stimulation can be applied to the stimulation electrode based on the data obtained by this real-time processing.

Figure 15:
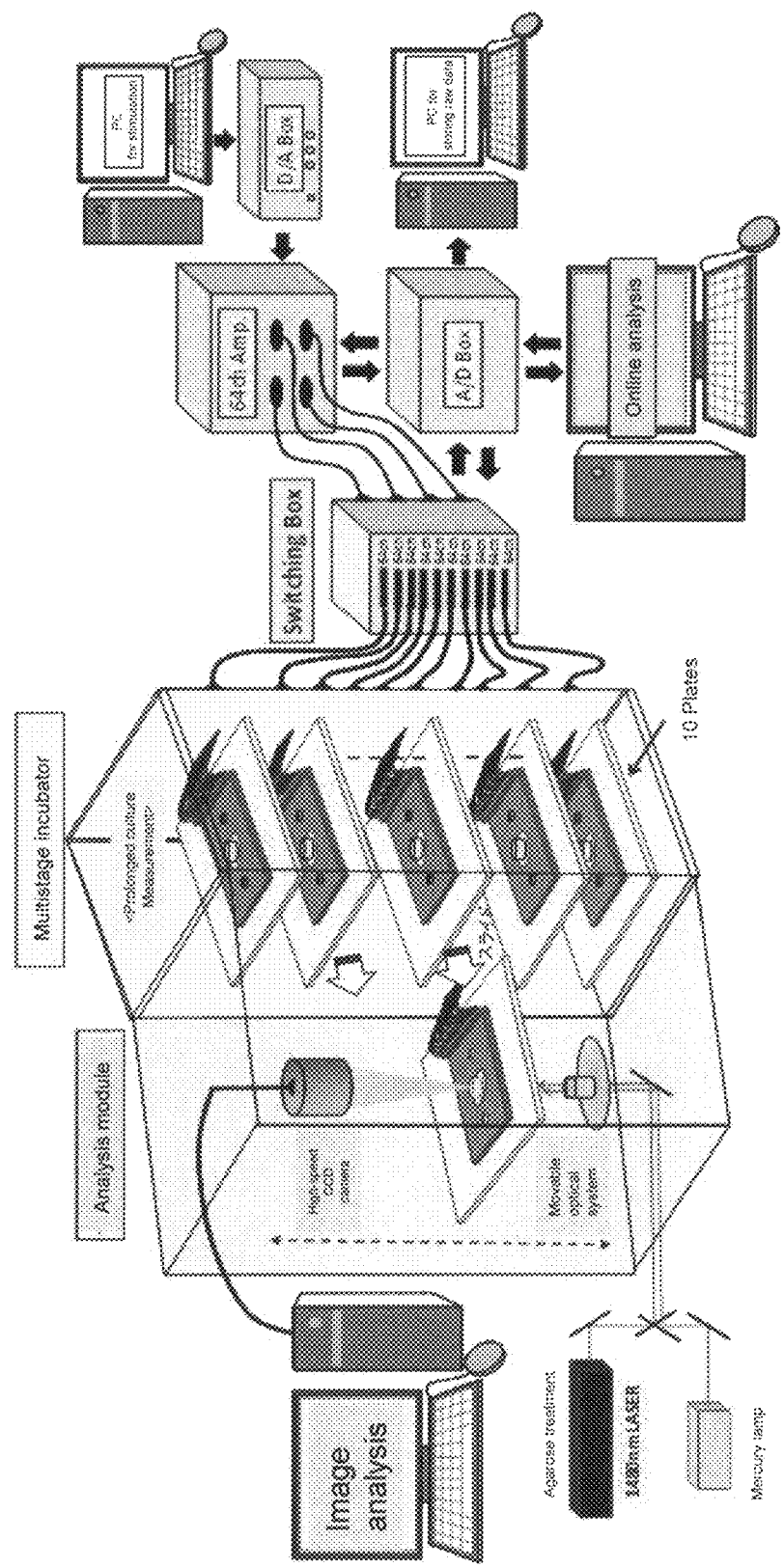
FIG. 15 is a schematic view for illustrating an exemplary mechanism for measuring a plurality of samples with a cell measurement system of the present invention.

FIG. 15 is a schematic view for illustrating an exemplary mechanism for measuring a plurality of samples with a cell measurement system of the present invention. The system of this example comprises an analysis module, a multistage incubator, an electroanalysis module and an online analysis module connected thereto via an online network. Here, the analysis module comprises a phase-contrast microscope or a differential interference microscope for measuring changes in the cellular shape, optical measurement means associated with a fluorescent microscope and a camera photography analysis, and an agarose processing technique that can locally dissolve agarose in micrometer scale with a microscopic system. Multiple cell culture baths are arranged in the multistage incubator, where microelectrode chips are arranged in the cell culture bath such that measurement of electric signals of each cell and electrical stimulation can be sequentially processed in parallel in the incubator. The obtained electric signals are subjected to real-time measurement in the electroanalysis module, and resulting data is recorded in a storage that is accessible online such that the results of optical measurement data and electric measurement data are recorded with the same time stamp. The analysis module can appropriately access to these record data online for analysis.

FIG. 16 is a schematic view for illustrating information of heart measured with a cell measurement system of the present invention. By electric signal measurement for a single cell on a microelectrode, signal data of ion channels such as Na-, Ca-, IKr- and IKs-ion channels can be measured and Na-ion channel inhibition can be measured by measuring the changes in the signal conduction velocities between adjacent myocardial cells. In addition, optical measurement of the change in the shape of a single cell allows measurement of generation of abnormal cardiac rhythm as well as estimation of cardiac output. Furthermore, generation of re-entry can be measured by circularly arranging the cell network. Moreover, measurement as a cardiac pathologic model such as cardiac hypertrophy can be realized by adding fibroblast cells to the cell arrangement.

INDUSTRIAL APPLICABILITY

According to the present invention, conduction response of cell pulsation of a cell communication channel CCC where myocardial cells and fibroblast cells are tandemly arranged and influence of a drug thereon, that is, myocardial toxicity of the drug, can be evaluated equivalently in vitro based on pulse of a cell population as a pacemaker.

DESCRIPTION OF REFERENCE NUMERALS

1: Transparent substrate, 2: microelectrode, 2c: comparison electrode, 2': readout line from microelectrode 2, $3_1$, $3_2$, $3_3$ and $3_4$: agarose gel walls, $4_1$, $4_2$, $4_3$ and $4_4$: gaps, 7: surrounding walls, $8_1$, $8_2$ and $8_3$: pipes, PC: personal computer, Ms: operation signal to personal computer, $10_0$, $10_1$, $10_2$, $10_3$, ... $10_n$: myocardial cells or fibroblast cells, 15: transparent stage for optical observation device, 16: X-Y driver, 18: Z driver, $CH_1$, $CH_2$, $CH_3$ and $CH_n$: cell holders, CCC: cell communication channel, $10_G$: cell population, $11_a$: barrier, $11_b$: opening, 19, 191, 192 and 193: diachronic mirrors, 20 and 201: bandpass filters, 21 and 211: cameras, 22: light source, 221: fluorescent light source, 23 and 231: bandpass filters, 24 and 241: shutters, 25: condenser lens, 26: objective lens, 27: movable electrode, 28: ground electrode, 29 and 291: switching circuit, 30 and 301: electric signal measurement circuits, 31 and 311: electrical stimulation circuits, 32: myocardial cell, 33: fibroblast cell, 34: pipette for cell arrangement, 35: N-th round of conduction pathway, 36: (N+1)-th round of conduction pathway, 37: (N+2)-th round of conduction pathway, 38: measuring electrode, 39: reference electrode, 40: solution sending system, 41: circularly-arranged cell population, 42: 96-well plate, 43: photo-sensitive element of the camera, 44: cell, 45: cell stimulation electrode, 100: myocardial toxicity examining device.

The invention claimed is:

1. A myocardial toxicity examining device comprising:
   a transparent substrate;
   a cell population comprising a plurality of stably-pulsating myocardial cells arranged on the transparent substrate;
   a cell communication channel comprising a tandemly-arranged plurality of myocardial cells and fibroblast cells which conduct pulse from the cell population in cooperation with one of the cells of the cell population;
   a surrounding wall that is formed on the transparent substrate and surrounds the cell population and the cell communication channel such that the region surrounded by the wall is to be filled with a cell culture solution;
   means for feeding and draining the cell culture solution into and from the region surrounded by the walls;
   means for adding a drug that acts on the cells to the cell culture solution;
   a microelectrode provided on the transparent substrate and having thereon one of the cells of the cell population;
   a plurality of separate microelectrodes provided on the transparent substrate and having thereon some of the cells of the cell communication channel;
   a comparison electrode provided within the region surrounded by the walls;
   means for measuring and recording potentials of the cells on the microelectrodes by using readout lines connected to the respective microelectrodes and a readout line connected to the comparison electrode; and
   means for optically measuring a state of one of the cells arranged on the transparent substrate.

2. The myocardial toxicity examining device according to claim 1, wherein the cell is surrounded by non-cell-adherent walls with gaps that do not allow the cell to pass therethrough.

3. The myocardial toxicity examining device according to claim 1 comprising a barrier between the region provided with the cell population and the region provided with the cell communication channel, for blocking the flow of the cell culture solution, where the barrier is provided with an opening that allows cooperation between one of the cells of the cell population and the cell at the end of the cell communication channel.

4. A myocardial toxicity examining device according to claim 1 comprising means for adding a drug that acts on the cells to means for feeding the cell culture solution.

5. A method for examining myocardial toxicity by using the myocardial toxicity examining device according to claim 1,
   wherein the method comprises the step of evaluating whether or not addition of a drug that acts on the cells to the cell culture solution delays the rate of the pulse generated by the cell population to propagate through the cell communication channel, thereby examining toxicity of the drug that acts on the cell on cardiac muscle.

6. The method for examining myocardial toxicity according to claim 5, comprising the step of quantitatively comparing the difference in pulse data between successive pulses of a certain cell to evaluate whether or not the fluctuation in that difference exceeds a certain value, thereby evaluating toxicity of a drug that acts on the cell on cardiac muscle.

7. The method for examining myocardial toxicity according to claim 5, wherein the cells are arranged in the circular cell network so as to obtain cell arrangement that allows selection among multiple conduction pathways, the method comprising the step of judging whether or not the conduction pathways differ among rounds, thereby evaluating toxicity of a drug that acts on the cell on cardiac muscle.

8. A myocardial toxicity examining device comprising:
   a transparent substrate;
   a cell population comprising a plurality of cells arranged on the transparent substrate;
   a cell communication channel comprising a tandemly-arranged plurality of myocardial cells and fibroblast cells which conduct pulse from the cell population in cooperation with one of the cells of the cell population;
   a surrounding wall that is formed on the transparent substrate and surrounds the cell population and the cell communication channel such that the region surrounded by the wall is to be filled with a cell culture solution;
   means for feeding and draining the cell culture solution into and from the region surrounded by the walls;
   means for adding a drug that acts on the cells to the cell culture solution;
   a microelectrode provided on the transparent substrate and having thereon one of the cells of the cell population;
   a plurality of separate microelectrodes provided on the transparent substrate and having thereon some of the cells of the cell communication channel;
   a comparison electrode provided within the region surrounded by the walls;
   means for measuring and recording potentials of the cells on the microelectrodes by using readout lines connected to the respective microelectrodes and a readout line connected to the comparison electrode; and
   a stage for supporting the transparent substrate, which can be driven in the X-Y directions; and
   means for optically measuring a state of the cell arranged on the transparent substrate supported by the stage.

9. A myocardial toxicity examining device according to claim 8, wherein the cell is surrounded by non-cell-adherent walls with gaps that do not allow the cell to pass therethrough.

10. The myocardial toxicity examining device according to claim 8 comprising a barrier between the region provided with the cell population and the region provided with the cell communication channel, for blocking the flow of the cell culture solution, where the barrier is provided with an opening that allows cooperation between one of the cells of the cell population and the cell at the end of the cell communication channel.

11. A myocardial toxicity examining device according to claim 8 comprising means for adding a drug that acts on the cells to means for feeding the cell culture solution.

* * * * *